United States Patent
Qiu et al.

(10) Patent No.: US 10,508,146 B2
(45) Date of Patent: Dec. 17, 2019

(54) SCFV-FC DIMERS THAT BIND TRANSFORMING GROWTH FACTOR-BETA1 WITH HIGH AFFINITY, AVIDITY AND SPECIFICITY

(71) Applicant: GENZYME CORPORATION, Cambridge, MA (US)

(72) Inventors: Huawei Qiu, Bridgewater, NJ (US); Clark Pan, Sudbury, MA (US); Julie Bird, Bridgewater, NJ (US)

(73) Assignee: GENZYME CORPORATION, Cambridge, MA (US)

( * ) Notice: Subject to any disclaimer, the term of this patent is extended or adjusted under 35 U.S.C. 154(b) by 0 days.

(21) Appl. No.: 15/555,499

(22) PCT Filed: Mar. 3, 2016

(86) PCT No.: PCT/US2016/020779
§ 371 (c)(1),
(2) Date: Sep. 2, 2017

(87) PCT Pub. No.: WO2016/141244
PCT Pub. Date: Sep. 9, 2016

(65) Prior Publication Data
US 2018/0222970 A1    Aug. 9, 2018

Related U.S. Application Data

(60) Provisional application No. 62/128,133, filed on Mar. 4, 2015.

(51) Int. Cl.
| | | |
|---|---|---|
| A61K 39/395 | (2006.01) | |
| C07K 16/22 | (2006.01) | |
| C07K 16/46 | (2006.01) | |
| C07K 16/00 | (2006.01) | |
| A61K 39/00 | (2006.01) | |

(52) U.S. Cl.
CPC ............ *C07K 16/22* (2013.01); *A61K 39/395* (2013.01); *A61K 39/3955* (2013.01); *C07K 16/00* (2013.01); *C07K 16/46* (2013.01); *A61K 2039/505* (2013.01); *C07K 2317/21* (2013.01); *C07K 2317/35* (2013.01); *C07K 2317/52* (2013.01); *C07K 2317/53* (2013.01); *C07K 2317/56* (2013.01); *C07K 2317/565* (2013.01); *C07K 2317/622* (2013.01); *C07K 2317/626* (2013.01); *C07K 2317/64* (2013.01); *C07K 2317/70* (2013.01); *C07K 2317/72* (2013.01); *C07K 2317/76* (2013.01); *C07K 2317/92* (2013.01); *C07K 2317/94* (2013.01); *C07K 2319/00* (2013.01); *C07K 2319/23* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 5,616,561 A | | 4/1997 | Barcellos-Hoff |
| 6,492,497 B1 * | | 12/2002 | Thompson ............. C07K 16/22 |
| | | | 424/142.1 |
| 7,151,169 B2 | | 12/2006 | Thompson et al. |
| 7,619,069 B2 | | 11/2009 | Davies et al. |
| 8,048,421 B2 | | 11/2011 | Kai et al. |
| 8,632,774 B2 | | 1/2014 | Misher et al. |
| 2002/0099179 A1 | | 7/2002 | Jolliffe et al. |
| 2008/0050375 A1 | | 2/2008 | Davies et al. |
| 2010/0174053 A1 | | 7/2010 | Johnson et al. |

FOREIGN PATENT DOCUMENTS

| | | | |
|---|---|---|---|
| EP | 1486560 | 12/2004 | |
| WO | 2000/066631 A1 | 11/2000 | |
| WO | WO-0066631 A1 * | 11/2000 | ............. C07K 16/22 |
| WO | 2004/098637 | 11/2004 | |
| WO | 2006/116002 | 11/2006 | |
| WO | 2007/109254 | 2/2007 | |
| WO | 2007/076391 | 7/2007 | |
| WO | WO 2012/088461 A2 * | 6/2012 | |
| WO | 2012/135345 A1 | 10/2012 | |
| WO | 2014/164709 | 10/2014 | |

OTHER PUBLICATIONS

Bujak et al., In: Ossipow V. and Fischer N. (eds) Monoclonal Antibodies. Methods in Molecular Biology (Methods and Protocols) (2014) vol. 1131, p. 315-334, e-pub: Jan. 24, 2014.*
Knappik et al., J. Mol. Biol., 2000, vol. 296(1):57-86.*
Yusakul et al., Biosci. Biotechnol. Biochem., 2016, vol. 80(7):1306-1312.*
Rispens et al., J. Biol. Chem., 2014, vol. 289(9):6098-6109.*
Aalberse et al., "IgG4 breaking the rules," Immunology 105:9-19 (2002).
Armour et al., "Recombinant human IgG molecules lacking Fcgamma receptor I binding and monocyte triggering activities," Eur J Immunol 29(8):2613-24 (1999).
Beck et al., "Strategies and challenges for the next generation of therapeutic antibodies," Nature Reviews, Immunology 10:345-352 (2010).
Bird et al., "Single-Chain Antigen-Binding Proteins," Science 242:423-426 (1988).
Border et al., "Suppression of experimental glomerulonephritis by antiserum against transforming growth factor β1," Nature 346:371-374 (1990).
Borsi et al., "Selective Targeting of Tumoral Vasculature: Comparison of Different Formats of an Antibody (L19) to the ED-B Domain of Fibronectin," Int. J. Cancer 102:75-85 (2002).

(Continued)

*Primary Examiner* — Xiaozhen Xie
(74) *Attorney, Agent, or Firm* — Steptoe & Johnson LLP; Z. Ying Li; Mauricio Alvarez

(57) ABSTRACT

An scFv-Fc dimer binds and neutralizes TGFβ1 selectively and with high affinity and avidity. The scFv region may comprise the same VH and VL domains or CDR regions as metelimumab. The unique combination of their smaller size, high selectivity, potency against TGFβ1, and long in vivo half-life makes the scFv-Fc dimers ideal candidates for therapeutic applications.

12 Claims, 5 Drawing Sheets

Specification includes a Sequence Listing.

(56) References Cited

OTHER PUBLICATIONS

Correa et al., "Structure of a human IgA1 Fab fragment at 1.55 Å resolution: potential effect of the constant domains on antigen-affinity modulation," Acta Crystallogr D Biol Crystallogr. 69(3):388-397 (2013).
Correa et al., "Structure of a human IgA1 Fab fragment at 1.55 Å resolution: potential effect of the constant domains on antigen-affinity modulation (supplementary figure S1)," Bioinformatics 1189-1191 (2009).
Datta-Mannan et al., "Humanized IgG1 variants with differential binding properties to the neonatal Fc receptor: relationship to pharmacokinetics in mice and primates," Drug Metab Dispos 35:86-94 (2007).
Giri et al., "Effect of antibody to transforming growth factor β on bleomycin induced accumulation of lungcollagen in mice," Thorax 48:959-966 (1993).
Grütter et al., "A cytokine-neutralizing antibody as a structural mimetic of 2 receptor interactions," Proc Natl Acad Sci USA 105(51):20251-6 (2008).
Harding et al., "The immunogenicity of humanized and fully human antibodies," mAbs 2(3):256-65 (2010).
Hieter et al., "Cloned human and mouse kappa immunoglobulin constant and J region genes conserve homology in functional segments," Cell 22(1):197-207 (1980).
Hinton et al., "Engineered Human IgG Antibodies with Longer Serum Half-lives in Primates," Chem 279(8):6213-6 (2004).
Holliger et al., "Engineered antibody fragments and the rise of single domains," Nat Biotechnol. 23:1126-1136 (2005).
Holmes et al., "Structural Consequences of Humanizing an Antibody," J Immunol 158(5):2192-201 (1997).
Huston et al., "Protein engineering of antibody binding sites: Recovery of specific activity in an anti-digoxin single-chain Fv analogue produced in *Escherichia coli*," Proc Natl Acad Sci USA 85(16):5879-83 (1988).
Idusogie et al., "Mapping of the C1q Binding Site on Rituxan, a Chimeric Antibody with a Human IgG1 Fc," J Immunol 164 (8):4178-84 (2000).
Idusogie et al., "Engineered Antibodies with Increased Activity to Recruit Complement," J Immunol 166(4):2571-5 (2001).
Katsumoto et al., "The Pathogenesis of Systemic Sclerosis," Annual Review of Pathology: Mechanisms of Disease, 6(1):509-537 (2011).
Labrijn et al., "Therapeutic IgG4 antibodies engage in Fab-arm exchange with endogenous human IgG4 in vivo," Nature Biotechnol 27:767-71 (2009).
Landolfi et al., "The integrity of the ball-and-socket joint between V and C domains is essential for complete activity of a humanized antibody." Journal of Immunology 166(3):1748-1754 (2001).
Lazar et al., "Engineered antibody Fc variants with enhanced effector function," Proc. Natl Acad. Sci. USA 103:4005-10 (2006).
Lesk et al., "Elbow motion in the immunoglobulins involves a molecular ball-and-socket joint," Nature 335:188-190 (1988).
Logan et al., "Effects of transforming growth factor beta 1 on scar production in the injured central nervous system of the rat," Eur J Neurosci 6:355-363 (1994).
Olafsen et al., "Antibody Vectors for Imaging," Semin Nucl Med 40:167-181 (2010).
Peters et al., "Engineering an Improved IgG4 Molecule with Reduced Disulfide Bond Heterogeneity and Increased Fab Domain Thermal Stability," Journal of Biological Chemistry 287(29):24525-24533 (2012).

Ponomarenko et al., "Role of [kappa]->[lambda] light-chain constant-domain switch in the structure and functionality of A17 reactibody," Acta Crystallogr D Biol Crystallogr 70(Pt 3):708-19 (2014).
Powers et al., "Expression of single-chain Fv-Fc fusions in Pichia pastoris," J Immunol Methods 251:123-135 (2001).
Richards et al., "Optimization of antibody binding to FcgammaRIIa enhances macrophage phagocytosis of tumor cells," Mol Cancer Ther 7(8) 2517-2527 (2008).
Ryan et al., "Antibody targeting of B-cell maturation antigen on malignant plasma cells," Mol Cancer Ther 6(11):3009-18 (2007).
Shah et al., "Control of scarring in adult wounds by neutralising antibody to transforming growth factor β," Lancet 339 (8787):213-4 (1992).
Shah et al., "Neutralising antibody to TGF-β1,2 reduces cutaneous scarring in adult rodents," J Cell Sci 107 (Pt 5):1137-57 (1994).
Shah et al., "Neutralisation of TGF-beta 1 and TGF-beta 2 or exogenous addition of TGF-beta 3 to cutaneous rat wounds reduces scarring," J. Cell Science 108:985-1002 (1995).
Shields et al., "High resolution mapping of the binding site on human IgG1 for Fc gamma RI, Fc gamma RII, Fc gamma RIII, and FcRn and design of IgG1 variants with improved binding to the Fc gamma R," J. Biol. Chem. 276:6591-604 (2001).
Stanfield et al., "Antibody Elbow Angles are Influenced by their Light Chain Class," Journal of Molecular Biology 357(5):1566-1574 (2006).
Steurer et al., "Ex vivo coating of islet cell allografts with murine CTLA4/Fc promotes graft tolerance," J. Immunol. 155:1165-74 (1995).
Strohl, "Optimization of Fc-mediated effector functions of monoclonal antibodies," Curr Opin Biotechnol. 20:685-91 (2009).
Vaccaro et al., "Engineering the Fc region of immunoglobulin G to modulate in vivo antibody levels," Nat Biotechnol. 23:1283-8 (2005).
Wahl et al., "Reversal of acute and chronic synovial inflammation by anti-transforming growth factor beta," Exp. Medicine 177:225-230 (1993).
Zhang et al., "Determination of Fab-Hinge Disulfide Connectivity in Structural Isoforms of a Recombinant Human Immunoglobulin G2 Antibody," Anal. Chem. 82:1090-99 (2010).
Rudikoff et al., "Single amino acid substitution altering antigen-binding specificity," Proc Natl Acad Sci U S A. 79(6):1979-83 (1982).
Sela-Culang et al., "The structural basis of antibody-antigen recognition," Front Immunol 4:302 (2013).
Berry et al., "Substitution of cysteine for selenocysteine in type I iodothyronine deiodinase reduces the catalytic efficiency of the protein but enhances its translation," Endocrinology. 131(4)1848-52 (1992).
Chen et al., "Enhancement and destruction of antibody function by somatic mutation: unequal occurrence is controlled by V gene combinatorial associations," EMBO J. 14(12):2784-94 (1995).
Colman, "Effects of amino acid sequence changes on antibody-antigen interactions," Res Immunol. 145(1):33-6 (1994).
Gasser et al., "Antibody production with yeasts and filamentous fungi: on the road to large scale?" Biotechnol Lett. 29(2):201-12 (2007).
Kussie et al., "A single engineered amino acid substitution changes antibody fine specificity," J Immunol. 152 (1):146-52(1994).
Alekperov, "treatment of systemic scleroderma," Russian Open Medical Journal (RusOMJ), No. 22 (2002).

\* cited by examiner

SCFV-FC DIMERS THAT BIND TRANSFORMING GROWTH FACTOR-BETA1 WITH HIGH AFFINITY, AVIDITY AND SPECIFICITY

RELATED APPLICATIONS

This patent application is a National Stage under 35 U.S.C. § 371 of International Application No. PCT/US2016/020779, filed Mar. 3. 2016, which claims the benefit of U.S. Provisional Patent Application No. 62/128,133, filed Mar. 4, 2015. The disclosures of both of the International Application and the Provisional Application are incorporated herein by reference in their entirety.

SEQUENCE LISTING

A sequence listing associated with this application is being submitted electronically via EFS-Web in text format, and is hereby incorporated by reference in its entirety into the specification. The name of the text file containing the Sequence Listing is 022548US017_Sequence_Listing.txt. The text file was created on Sep. 2, 2017 and is 32,353 bytes in size.

BACKGROUND OF THE INVENTION

Technical Field

An antigen-binding dimer having two polypeptide monomers, each comprising a single-chain fragment variable molecule (scFv), a hinge, and an Fc molecule, exhibits high affinity and avidity to Transforming Growth Factor-β1 (TGFβ1) but not to TGFβ2 or to TGFβ3. Compositions comprising the antigen-binding dimer and methods of using the same for treatment of diseases involving TGFβ1 activity are provided.

Background

Many severe diseases are linked to malfunctions of the TGFβ-induced signaling pathway. For instance, an increased tissue level of TGFβ is believed to be a factor in the development of idiopathic pulmonary fibrosis and myocardial fibrosis. Furthermore, high local tissue levels of TGFβ may allow the maintenance and progression of some types of cancer cells. Down-regulation of TGFβ signaling therefore may reduce the viability of such tumor cells.

TGFβ isoforms are ~25 kDa homodimeric molecules with a similar structural framework in which two monomers are covalently linked via a disulfide bridge. The mammalian isoforms share a sequence identity of 70-82%, but have non-overlapping activities in vascular development and the regulation of immune cell function. Three TGFβ isoforms have been reported in humans: TGFβ1, TGFβ2, and TGFβ3 (Swiss Prot accession numbers P01137, P08112, and P10600, respectively). TGFβ1 and TGFβ3 trigger a cellular signaling cascade upon binding to the extracellular domains of two transmembrane receptors, known as TGFβ receptor types I and II. TGFβ2 may bind to TGFβ receptor types I and II, as well as TGFβ receptor type III.

Antibodies that can bind human TGFβ1, TGFβ2, and TGFβ3 have been tested for clinical use. For instance, Grütter et al. disclosed GC1008, a human IgG4 monoclonal antibody (Mab; i.e., GC1008) in clinical development for treating malignancy and fibrotic diseases. *Proc. Nat'l Acad. Sci. USA* 105(51): 20251-56 (2008). GC1008 is a "pan-specific" TGFβ neutralizing antibody, because it can neutralize all three human TGFβ isoforms. Antibodies that selectively neutralize TGFβ1 are disclosed, for example, in U.S. Pat. Nos. 6,492,497 and 7,151,169, which are incorporated by reference into this disclosure. Metelimumab, also known as CAT192 (IgG4), is a human IgG4 monoclonal antibody that selectively neutralizes TGF-β1. See e.g., U.S. Pat. No. 6,492,497. Metelimumab was tested for the treatment of diffuse cutaneous systemic sclerosis, also known as scleroderma, but demonstrated insufficient efficacy.

BRIEF SUMMARY OF THE INVENTION

The present disclosure provides TGFβ1-binding scFv-Fc dimers that are capable of selectively neutralizing human TGFβ1. In one embodiment, the scFv-Fc dimers are formatted as scFv-Fc fusion proteins comprised of two polypeptide monomers, each monomer comprising a single-chain Fv region (scFv), a hinge, and an Fc region. The VH and VL domains of the scFv-Fc dimer exhibit a higher affinity and avidity to TGFβ1 and more effectively neutralize TGFβ1 than when used in the IgG1 or IgG4 format.

In one embodiment, the scFv component may be composed of the same VH and VL domains as the VH and VL domains of metelimumab. The variable domains in the scFv component may be linked together by a linker, e.g., a $[G_4S]_3$-type linker. Each of the scFv components of the scFv-Fc dimers may be fused via a hinge region, e.g., a human IgG1 or IgG4 hinge region, to an Fc region. The monomers of the dimer may be covalently linked by a disulfide bond between cysteine residues in the hinge region. In another embodiment, the scFv-Fc dimers may have structural dissimilarities to metelimumab, most notably the absence of $CH_1$ and CL domains and the presence of a linker between the VH and VL domains. Advantageously, the scFv-Fc dimers display an apparent affinity toward TGFβ1 nearly two orders of magnitude greater than that of an scFv comprising the same VH and VL domains (CAT191(scFv), shown in SEQ ID NO: 12) in an A549 cell potency bioassay. Further, the scFv-Fc dimers display an apparent affinity toward TGFβ1 over three orders of magnitude greater than that of an IgG-formatted antibody comprising the same VH and VL domains (e.g., CAT192) in the A549 cell bioassay. The scFv-Fc dimers also display desirable stability and pharmacokinetic properties. Because of their relatively small size and extended half-life in serum, the scFv-Fc dimers are particularly useful for therapeutic applications.

Accordingly, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ2, as measured by surface plasmon resonance.

In another embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ3, as measured by surface plasmon resonance.

In a further embodiment, the present invention is directed to an isolated binding protein comprising a variable domain that is capable of binding TGFβ1, wherein the binding protein exhibits a Kd for human TGFβ1 at least about 50% lower than the Kd of the same binding protein for human TGFβ2, and at least about 50% lower than the Kd of the same binding protein for human TGFβ3, as measured by surface plasmon resonance.

In a further embodiment, the present invention is directed to an isolated binding protein that binds TGFβ1, wherein the binding protein comprises a first polypeptide chain and a second polypeptide chain, the first and the second polypeptide chains each having the formula of:

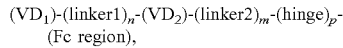

wherein $VD_1$ comprises a first variable domain selected from the group consisting of a VL domain isolated from an antibody capable of binding TGFβ1, and a VH domain isolated from an antibody capable of binding TGFβ1, and VD2 comprises a second variable domain selected from the group consisting of a VL domain isolated from an antibody capable of binding TGF β1, and a VH domain isolated from an antibody capable of binding TGFβ1; and wherein, n is 0 or 1, m is 0 or 1, and p is 0 or 1.

In one embodiment, the present invention is directed to an isolated TGFβ1-binding scFv-Fc dimer that selectively binds TGFβ1. The scFv-Fc dimer may comprise two polypeptide monomers, each having the following formula, from N-terminal to C-terminal: (VH domain)-(linker)-(VL domain)-(hinge)-(Fc region). In another embodiment, an isolated binding protein that binds TGFβ1 is disclosed, which comprises a first polypeptide chain and a second polypeptide chain. The first and the second polypeptide chains may both have the formula of, from N-terminal to C-terminal: (VH domain)-(linker1)$_n$-(VL domain)-(linker2)$_m$-(hinge)$_p$-(Fc region). p may be 0 or 1, n may be 0 or 1, and m may be 0 or 1. In one aspect, the first and second polypeptide chains may be identical and may form a dimer.

In another embodiment, the disclosed TGFβ1 binding protein may comprise a polypeptide chain having the formula of, from N-terminal to C-terminal: (VH domain)-(linker1)$_n$-(VL domain)-(linker2)$_m$-(hinge)$_p$-(Fc region), wherein p may be 0 or 1, n may be 0 or 1, and m may be 0 or 1.

The VH domain of the disclosed binding protein may comprise a variable heavy complementarity determining region 1 (HCDR1), a variable heavy complementarity determining region 2 (HCDR2), and a variable heavy complementarity determining region 3 (HCDR3). In one aspect, the HCDR1 may have the amino acid sequence of SEQ ID NO: 22, The HCDR2 may have the amino acid sequence of SEQ ID NO: 23, and the HCDR3 may have the amino acid sequence of SEQ ID NO: 24, SEQ ID NO: 25, SEQ ID NO: 26, or SEQ ID NO: 30.

The framework regions of the VH domain may be selected from a variable heavy germline sequence. The VH domain may be selected, for example, from the human VH domain sequences set forth in SEQ ID NO: 1 or SEQ ID NO: 2, or a variant thereof having modifications in up to four amino acids.

The VL domain of the disclosed binding protein may comprise a variable light complementarity determining region 1 (LCDR1), a variable light complementarity determining region 2 (LCDR2), and a variable light complementarity determining region 3 (LCDR3). In one aspect, the LCDR1 may have the amino acid sequence of SEQ ID NO: 27, the LCDR2 may have the amino acid sequence of SEQ ID NO: 28, and the LCDR3 may have the amino acid sequence of SEQ ID NO: 29.

The framework regions of the VL domain may be selected from a variable lambda or kappa germline sequence. The VL domain may be selected, for example, from the human Vκc domain sequences set forth in SEQ ID NO: 5 or SEQ ID NO: 6, or a variant thereof having modifications of up to four amino acids. In one embodiment, each polypeptide of the dimer may comprise the VH domain set forth in SEQ ID NO: 1 and the Vκc domain set forth in SEQ ID NO: 5, which are the VH and VL domains present in metelimumab, respectively.

In one embodiment, the variable domains in the scFv component may be linked by a flexible linker about 15 amino acids in length. "About" in this context means the linker can vary by up to plus or minus four amino acids in length. For optimal flexibility, the linker is composed predominantly of glycine and serine residues. For example, the linker may be a [G$_4$S]$_3$-type linker. The linker may have the amino acid sequence SGGGSGGGGSGGGGS (SEQ ID NO: 3), the amino acid sequence GGGGSGGGGSGGGGS (SEQ ID NO: 4), or a variant thereof having up to four amino acid modifications. For purpose of this disclosure, "having up to x amino acids modifications" means that the up to x number of amino acids may be changed to different amino acids by one of skill in the art without significantly altering the structure and function of the polypeptide.

In another embodiment, p is 1 and the scFv component is connected to an Fc region by a hinge. The hinge may comprise amino acid sequences derived from a human IgG1 or IgG4 hinge region. For example, the hinge may comprise the amino acid sequence PKSCDKTHTCPPCPAPELLGGP (SEQ ID NO: 7), or a variant thereof having up to four amino acid modifications. In one embodiment, the hinge length may vary from 3-15 amino acids. When the hinge is from a human IgG1, it may comprise the amino acid sequence CPPCP (SEQ ID NO: 21). Further, the variant of the hinge of SEQ ID NO: 7, which is also a human IgG1 hinge, may comprise the amino acid sequence CPPCP (SEQ ID NO: 21).

In another embodiment, m is 1 and a linker2 is present between scFv component and the hinge. In one aspect, linker2 may comprise the amino acid sequence GGSG (SEQ ID NO: 20), or a variant thereof having up to 2 amino acid modifications.

The Fc region may comprise two or three constant domains, e.g., a $CH_2$ domain and $CH_3$ domain. The Fc region may be obtained from a human IgG1, a human IgG4, or a variant of a human IgG1 or IgG4 having up to ten amino acid modifications, for example. In one embodiment, each polypeptide of the dimer has the sequence set forth in SEQ ID NO: 9. The structure of the scFv-Fc dimer of SEQ ID NO: 9 is shown in FIG. 2. The scFv-Fc dimer may bind TGFβ1 selectively. The scFv-Fc dimer may show an apparent dissociation constant less than 1 nM or even less than 0.1 nM. The apparent dissociation constant may be measured by using an A549 bioassay or by surface plasmon resonance, for example.

In another embodiment, an isolated polynucleotide is disclosed which may comprise a nucleotide sequence encoding the scFv-Fc dimer. The isolated polynucleotide may be a cDNA, a recombinant DNA or a synthetic DNA. A host cell may comprise the isolated nucleic acid. The host cell may be a human cell, such as a Human Embryonic Kidney 293 (HEK293) cell and cell lines derived therefrom, or it may be a Chinese Hamster Ovary (CHO) cell. A method of making the scFv-Fc dimer may include culturing the host cell under suitable conditions to produce the scFv-Fc dimer. The scFv-Fc dimer may be purified. The degree of purity may be 90%, 95%, 99%, 99.5% or more.

The scFv-Fc dimer of the present invention may be an element of a composition. The composition may be a pharmaceutical composition. The pharmaceutical composition may comprise a therapeutically effective amount of the scFv-Fc dimer. The composition may further comprise one or more biologically active components, excipients, or diluents.

A method of treating a disease or condition resulting directly or indirectly from TGFβ1 activity in a human may comprise administering a pharmaceutical composition comprising a therapeutically effective amount of the scFv-Fc dimer. The disease or condition may be selected from the group consisting of a fibrotic disease, cancer, an immune-mediated disease, e.g., diffuse cutaneous systemic sclerosis, bone remodeling disease, kidney disease and/or combinations thereof. The scFv-Fc dimer may be used in the manufacture of a medicament for treatment of a disease or disorder selected from the group consisting of a fibrotic disease, cancer, an immune-mediated disease, e.g., diffuse cutaneous systemic sclerosis, bone remodeling disease, kidney disease and/or combinations thereof. The treatment of the disease or disorder may comprise neutralizing TGFβ1 or inhibiting TGFβ1 signaling. The treatment of the disease or disorder may comprise inhibiting TGFβ1-mediated fibronectin production, vascular endothelial growth factor (VEGF) production, epithelial cell proliferation, endothelial cell proliferation, smooth muscle cell proliferation, or immunosuppression. The treatment of the disease or disorder may comprise increasing natural killer cell activity.

BRIEF DESCRIPTION OF THE SEVERAL VIEWS OF THE DRAWING(S)

The drawings presented herein are for purpose of illustration and are not to be used to limit the scope of the present invention.

Figure 3:
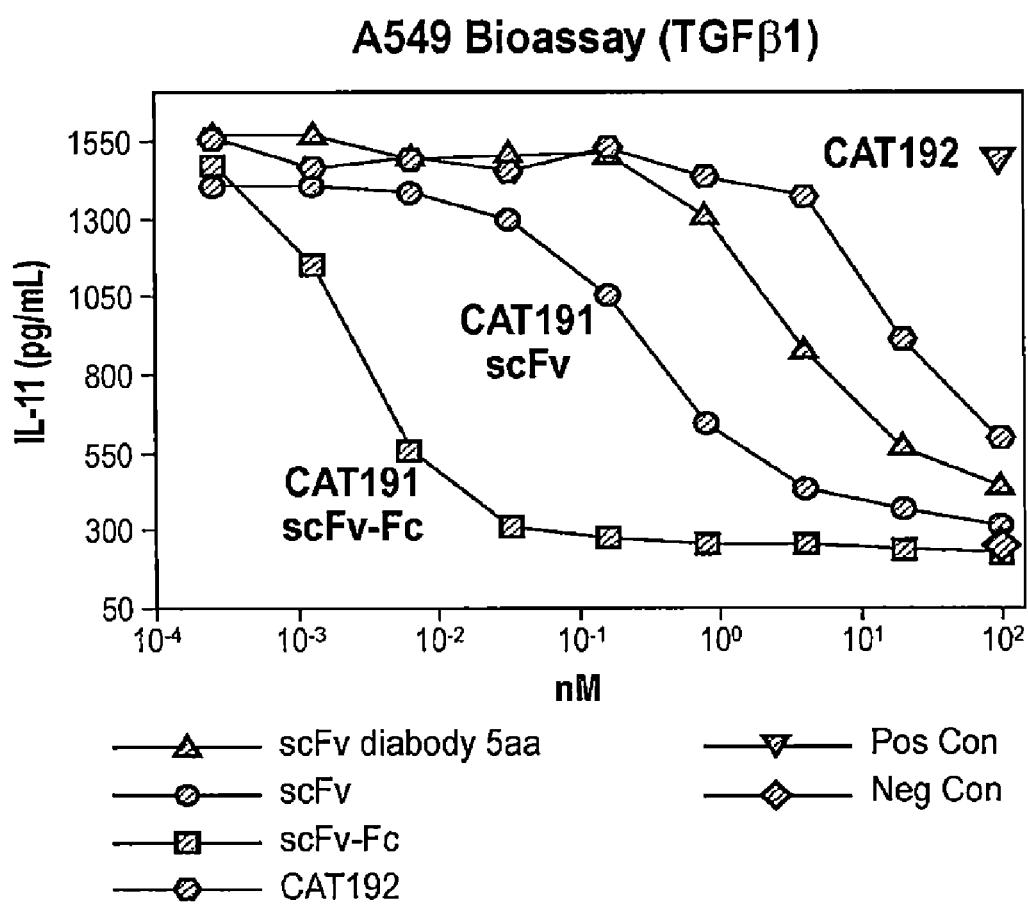

FIG. 3 shows the results of an A549 cell bioassay comparing the inhibitory effects by various antibody constructs on TGFβ1-stimulated IL-11 production: scFv diabody 5aa (SEQ ID NO: 14); CAT191(scFv) (SEQ ID NO: 12); CAT191(scFv-Fc) (SEQ ID NO: 9); and CAT192(IgG4) (light chain SEQ ID NO: 10 and heavy chain SEQ ID NO: 11).

Figure 4:
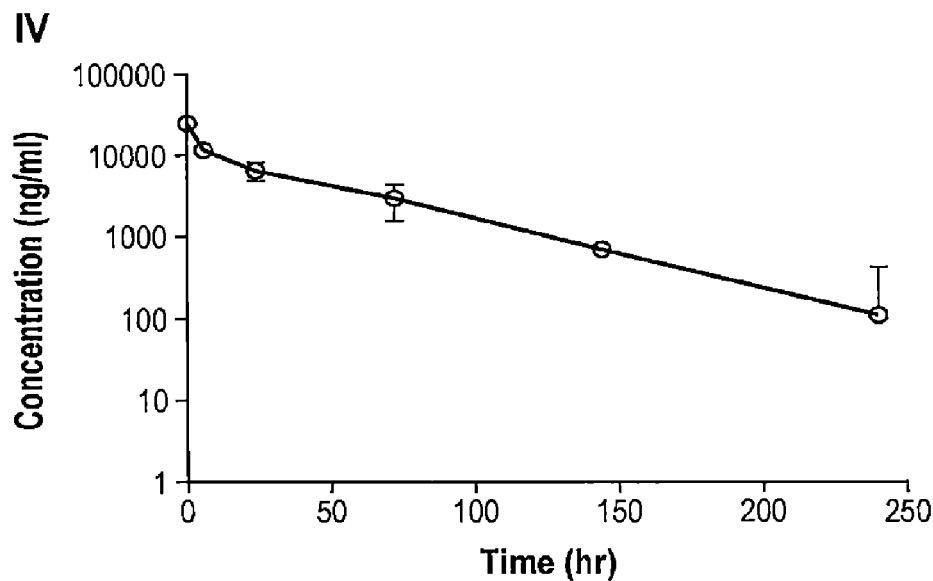

FIG. 4 depicts the results of pharmacokinetic tests to determine the half-life of CAT191 (scFv-Fc) following intravenous (IV) administration.

Figure 5:
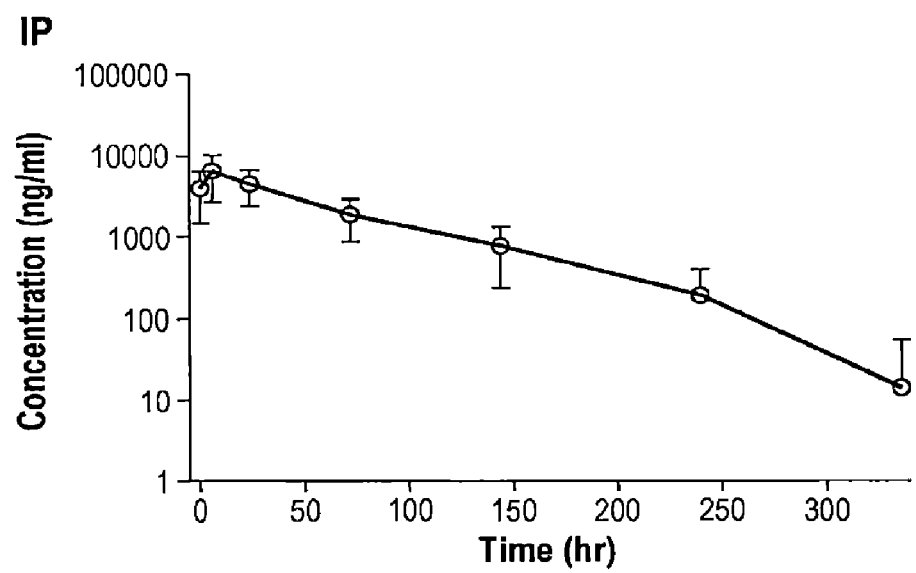

FIG. 5 depicts the results of pharmacokinetic tests to determine the half-life of CAT191 (scFv-Fc) following intraperitoneal (IP) administration.

Figure 6:
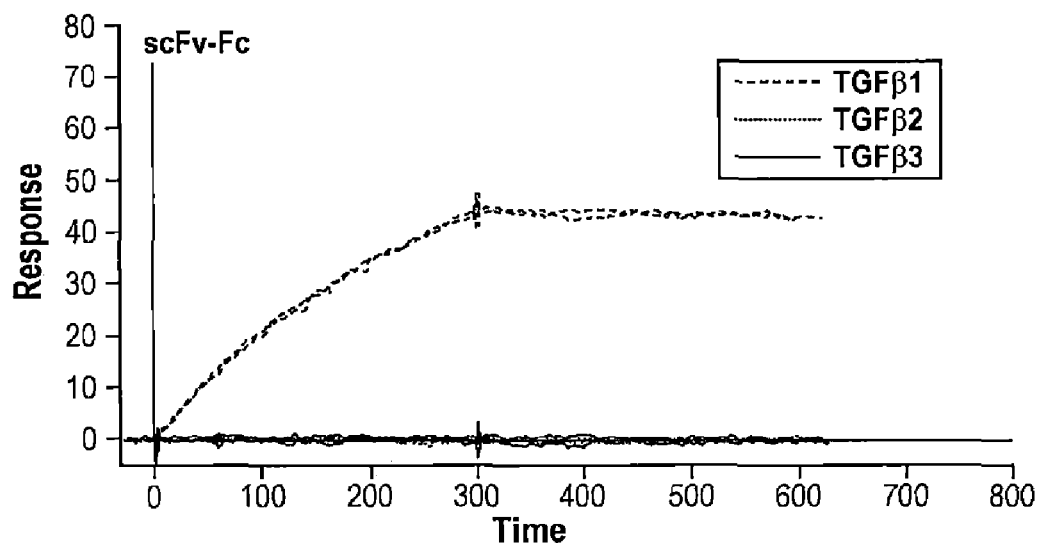

FIG. 6 shows the TGFβ1-specific binding results of CAT191(scFv-Fc) prepared from CHO cells.

Figure 7:
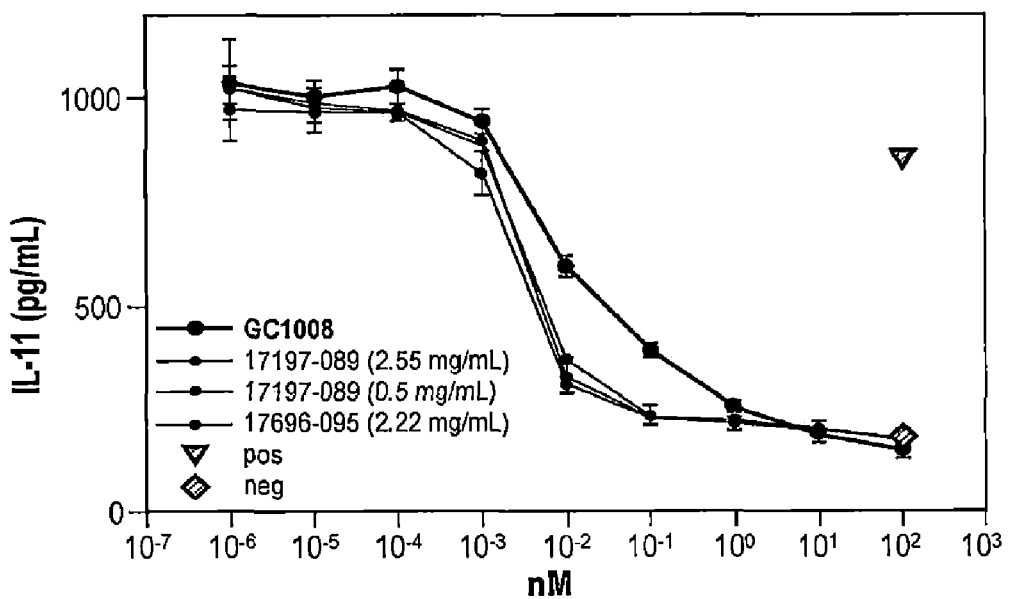

FIG. 7 shows the cell-based potency assay results of CAT191(scFv-Fc) prepared from CHO cells.

DETAILED DESCRIPTION OF THE INVENTION

The disclosed scFv-Fc dimers bind and neutralize TGFβ1 selectively and with high affinity and avidity. The scFv regions may be composed of the same VH and VL domains as in metelimumab. scFv-Fc dimers advantageously show greater efficacy in neutralizing TGFβ1 than when the variable domains are used in other formats. Because of their relatively small size and extended half-life in serum, the present scFv-Fc dimers are ideal candidates for therapeutic applications.

As used herein, a first element "and/or" a second element means a specific disclosure of the first or second element separately, or the first and second elements in combination. The singular forms "a," "an," and "the" include plural referents unless the context clearly dictates otherwise.

An "isolated" polynucleotide (or nucleic acid) or protein is removed and/or altered from its natural form using genetic engineering technologies. A "purified" nucleic acid or protein may be substantially pure, e.g., at least 90% pure, or in homogeneous form.

"Selective binding", or "binding selectively" to human TGFβ1, means that the binding protein (e.g., scFv-Fc dimer) is capable of binding human TGFβ1 with a higher affinity than binding to human TGFβ2 or human TGFβ3, e.g., with a dissociation constant with human TGFβ1 at least 50% lower than its dissociation constant with human TGFβ2 or human TGFβ3, as measured by surface plasmon resonance.

scFv-Fc Dimers

In one embodiment, the present scFv-Fc dimer variable domains comprise complementarity determining regions (CDRs) from the CDRs disclosed in U.S. Pat. No. 6,492,497 (e.g., SEQ ID NOs: 11-19 of U.S. Pat. No. 6,492,497), incorporated herein by reference. The CDR regions are listed below:

| | |
|---|---|
| HCDR1 | SEQ ID No. 22 |
| SYGMH | |
| HCDR2 | SEQ ID No. 23 |
| VISYDGSIKYYADSVKG | |
| HCDR3 | SEQ ID No. 24 |
| TGEYSGYDTSGVEL | |
| | SEQ ID No. 25 |
| TGEYSGYDTDPQYS | |
| | SEQ ID No. 26 |
| TGFYSGYDTPASPD | |
| LCDR1 | SEQ ID No. 27 |
| RASQGIGDDLG | |
| LCDR2 | SEQ ID No. 28 |
| GTSTLQS | |
| LCDR3 | SEQ ID No. 29 |
| LQDSNYPLT | |

Surprisingly, a consensus HCDR3 binding motif is revealed, having the sequence:

| | SEQ ID No. 30 |
|---|---|
| HCDR3 | TGX$_1$YSGYDTX$_2$X$_3$X$_4$X$_5$X$_6$ |

Wherein: X$_1$ may be any amino acid (preferably E, or F), or absent,

X$_2$ may be any amino acid (preferably S, D, or P), or absent,

X$_3$ may be any amino acid (preferably G, P, or A), or absent,

X$_4$ may be any amino acid (preferably V, Q, or S), or absent,

X$_5$ may be any amino acid (preferably E, Y, or P), or absent,

X₆ may be any amino acid (preferably L, S, or D), or absent.

The VH domain comprises the HCDR1 of SEQ ID No. 22, the HCDR2 of SEQ ID No. 23, and one of the HCDR3s selected from the group consisting of SEQ ID No. 24, SEQ ID No. 25, SEQ ID No. 26, and SEQ ID No. 30. The CDR sequences may be separated by anywhere from one to four framework regions, in order from the N-terminal: FW1-CDR1-FW2-CDR2-FW3-CDR3-FW4. The framework regions of the VH domain may be selected from a variable heavy germline sequence. In one embodiment, the FW region sequences may be selected from the same human variable heavy germline sequence. The VL domain comprises the LCDR1 of SEQ ID NO: 7, the LCDR2 of SEQ ID NO: 28, and the LCDR3 of SEQ ID NO: 29. The framework regions of the VL domain may be selected from a variable lambda or kappa germline sequence, e.g., from the same human variable lambda or kappa germline sequence. At present, about 40 variable heavy germline sequences are known in the art, as are about 40 variable kappa germline sequences and about 30 variable lambda germline sequences, e.g., $V_H3$, $V_\kappa 1$, $V_H 1$-69, and $V_H 1$-e.

In another embodiment, composite VH or VL domains may be generated by using the CDR sequences disclosed herein. For example, crystal structures of the VH or VL domains may be used as a guidance to generate composite domain using CDR sequences from one antibody and using the germline FW regions from another antibody. More details can be found in U.S. Patent Application Publication No. 20020099179; and Homes and Foote, J Immunol. 1997 Mar. 1; 158(5): 2192-201, both of which are hereby incorporated into this disclosure by reference.

The present scFv-Fc dimers may be composed of the same VH and VL domains as in metelimumab, having the sequences set forth in SEQ ID NO: 1 and SEQ ID NO: 5, respectively. The VH domain may be replaced by the VH domain having the sequences set forth in SEQ ID NO: 2; the VL domain may be replaced by the VL domain having the sequences set forth in SEQ ID NO: 6. These VH and VL domains are disclosed in U.S. Pat. No. 6,492,497 (e.g., SEQ ID NOS: 4, 6, 8, and 10), incorporated herein by reference.

A "variable domain" (VD) refers to a hypervariable binding domain of an immunoglobulin, or a ligand binding domain of a receptor, involved in antigen/ligand binding as is known by persons skilled in the art. Variable domains are routinely referred to by their location or origin within an immunoglobulin; e.g., variable domains of the light chain of an immunoglobulin (VL), variable domains of the heavy chain of an immunoglobulin (VH), variable domains of the heavy chain of a camelid immunoglobulin (VHH).

A "variant" variable domain comprises amino acid additions, substitutions, and/or deletions, compared to the reference sequence. A "variant" of the VH or VL domains may have up to four such amino acid modifications. For example, one of the two domains may comprise an amino acid substitution, while the other domain is unmodified, or both of the domains may comprise amino acid substitutions. Modifications that add or delete amino acid residues may be made at the N-terminus or C-terminus of the VH or VL domain. For example, the N-terminal residue of the VH domain may be deleted.

Up to four amino acid substitutions may be made to de-immunize the scFv-Fc dimer, for example. De-immunization can be performed according to the method of Harding et al. (2010) *mAbs* 2: 256-265, for example.

Framework residues of the VH and/or VL domains, for example, may be substituted to increase the stability of the scFv-Fc dimers and/or decrease their tendency to aggregate. Poor stability can affect the ability of the expressed scFv-Fc dimers to fold properly when recombinantly expressed, resulting in a fraction of the expressed antibodies being non-functional. Low stability antibodies also may be prone to forming potentially immunogenic aggregates or may have impaired avidity or shelf-life. scFv polypeptides in particular may demonstrate problems with stability, solubility, expression, aggregation, breakdown products, and overall manufacturability in both bacterial and mammalian expression systems. Framework amino acid substitutions that are expected to increase the stability and/or decrease the tendency to aggregate of a VH and/or VL domain, e.g., in an scFv polypeptide, are disclosed in WO 2007/109254, for example. Substitutions in corresponding residues in the present VH and VL domains are expected similarly to increase stability and/or decrease the tendency of scFv-Fc dimers to aggregate.

Substitutions that can be tolerated are expected to include those that would replace an amino acid of SEQ ID NO: 1, 2, 5, or 6 with a corresponding amino acid that occurs in another human VH or VL domain germline sequence. A substitution of a framework amino acid with an amino acid occurring in any of these germline sequences may be tolerated. For example, a residue of a VH domain of SEQ ID NO: 1 could be substituted with an amino acid appearing in a corresponding position in any VH germline sequence, e.g., the germline sequence from DP-10 ($V_H 1$-69) or DP-88 ($V_H 1$-e). Corresponding positions in this case are determined by a sequence alignment between the various germline sequences, using alignment techniques well known in the art, e.g., ClustalW.

Additional substitutions that are expected to be tolerated are those made to an amino acid with most of its side chain exposed to the solvent, as determined by analysis of the three co-crystal structures. The solvent-accessible surface area of a residue may be estimated using techniques well known in the art. Further, it is expected that substitutions to amino acids buried within the variable domains will be better tolerated if the side chain of the amino acid does not create steric hindrance with adjoining residues. For this reason, buried amino acids generally are substituted with amino acids with side chains of similar or smaller size. For example, a substitution of a buried Ile residue with a Leu, Val, Ala, or Gly is expected to be tolerated. Possible steric hindrance created by a substitution can be predicted by analysis of the three co-crystal structures. Further substitutions that are expected to be tolerated are those maintaining existing electrostatic interactions within the variable domains, e.g., dipole-dipole interactions, induced dipole interactions, hydrogen bonds, or ionic bonds.

Additional amino acid substitutions of variable domains include those expected to confer new useful properties to the antibodies or antigen-binding fragments thereof. For example, putative N-glycosylation sites in the VH and/or VL domains can be removed to prevent or reduce the formation of N-glycoforms. The amino-terminal residue can be substituted with a Gln residue to cause pyroglutamylation, which can decrease the number of charge variants. Amino acid substitutions can be used to lower the isoelectric point, which can decrease the rate of elimination of IgG polypeptide antibodies for example.

Surface residues of variable domains can be substituted with Cys or Lys residues, for example, which then can be covalently modified and coupled to molecules conferring useful characteristics to the antibodies or antigen-binding fragments thereof, e.g., a detectable label, toxin, targeting moiety, or protein. For example, Cys residue can be coupled to a cytotoxic drug to form a drug conjugate. Cys residues also can be coupled to molecules that increase the serum half-life, e.g., polyethylene glycol (PEG) or serum albumin. Such amino acid modifications are reviewed in Beck et al. (2010) *Nature* 10: 345-52, for example.

Detectable labels include radiolabels such as $^{131}$I or $^{99}$Tc, which may be attached to antibodies or antigen-binding fragments thereof using methods known in the art. Labels also include enzyme labels such as horseradish peroxidase. Labels further include chemical moieties such as biotin which may be detected via binding to a specific cognate detectable moiety, e.g., labeled avidin. Other moieties can be attached that facilitate purification. For example, antibodies or antigen-binding fragments thereof can be His-tagged using well-known methods of recombinant modification and expression.

The VH and VL domains of the scFv-Fc dimers are linked together by a linker, termed Linker1 herein. Linkers suitable for making an scFv fragment are well known in the art. See, e.g., Bird et al. (1988) *Science*, 242: 423-426; Huston et al. (1988) *Proc. Nat'l Acad. Sci. USA* 85: 5879-5883. This can be accomplished by fusing the encoding nucleic acids in-frame and expressing the fusion protein in a suitable host cell, for example. Suitable linkers include those of the $[G_4S]_3$-type. The $[G_4S]_3$-type linkers are composed of repeating units of glycine and serine residues. Such linkers may have a sequence of SGGGSGGGGSGGGGS (SEQ ID NO: 3) or GGGGSGGGGSGGGGS (SEQ ID NO: 4) or a variant thereof having up to four amino acid modifications, for example. Modifications can include deletions or insertions that change the linker length, or amino acid substitutions, preferably from Gly to Ser or vice versa. $[G_4S]_3$-type linkers have been widely used to link variable domains in an scFv structure, because the linkers are hypoallergenic and causes minimal conformational distortions to the variable domains. See, e.g., Huston et al. (1988) *Proc. Natl. Acad. Sci. USA* 85: 5879-83.

In the scFv-Fc dimers, a short linker sequence, termed Linker2 herein, is optionally inserted between the VL domain and the hinge. This linker sequence increases the flexibility of the scFv component with respect to the Fc component. In one embodiment, Linker2 has the sequence of GGSG (SEQ ID NO: 20). Suitable modifications to the GGSG linker include altering its length by one to four amino acids or substituting one to two amino acids, preferably from Gly to Ser or vice versa.

The hinge region is a flexible domain that joins the scFv portion to the Fc region. The flexibility of the hinge region in IgG and IgA molecules allows the Fab arms to adopt a wide range of angles, permitting binding to epitopes spaced variable distances apart. A suitable hinge region includes, for example, the human IgG1 hinge region having the amino acid sequence PKSCDKTHTCPPCPAPELLGGP (SEQ ID NO: 7). This sequence corresponds to a portion of the human IgG1 upper hinge, the middle hinge, and an N-terminal portion of the CH$_2$ domain, as disclosed in FIG. 4B of U.S. Pat. No. 8,048,421, for example. The hinge from a human IgG1 contains two Cys residues, which can form disulfide bonds with the Cys residues of the hinge on the corresponding monomer. The human IgG1 hinge portion that forms the disulfide bonds contains the amino acid sequence CPPCP (SEQ ID NO: 21). Variants of a human IgG1 hinge may comprise this sequence.

The scFv component is fused in frame to an Fc region, which forms the Fc component of the dimer. Suitable Fc regions contain two or three constant regions. Fc regions include those from human IgG1, as set forth in SEQ ID NO: 8, or IgG4, as set forth in the CH$_2$ and CH$_3$ domains of SEQ ID NO: 11. The Fc region of an antibody mediates its serum half-life and effector functions, such as complement-dependent cytotoxicity (CDC), antibody-dependent cellular cytotoxicity (ADCC) and antibody-dependent cell phagocytosis (ADCP).

Modifications can be made to the hinge and Fc region to improve various properties of the scFv-Fc dimers. In one embodiment, one, two, three, four, five or up to ten amino acids of a naturally occurring human Fc region can be modified, in addition to modifications of the hinge region. For example, the Fc region can be modified to increase the serum half-life of the scFv-Fc dimer. The half-life of an IgG depends on its pH-dependent binding to the receptor FcRn. FcRn, which is expressed on the surface of endothelial cells, binds the IgG in a pH-dependent manner and protects it from degradation. Mutations located at the interface between the CH2 and CH3 domains, for example, have been shown to increase the binding affinity to FcRn and the half-life of IgG1 in vivo. Such modifications are reviewed in Strohl W R., 2009. Optimization of Fc-mediated effector functions of monoclonal antibodies. Curr Opin Biotechnol. 20(6): 685-91; and Vaccaro C. et al., 2005. Engineering the Fc region of immunoglobulin G to modulate in vivo antibody levels. Nat Biotechnol. 23(10): 1283-8, for example.

Other modifications to the hinge and/or Fc region can increase or reduce effector functions. The four human IgG isotypes bind the activating Fcγ receptors (FcγRI, FcγRIIa, FcγRIIIa), the inhibitory FcγRIIb receptor, and the first component of complement (C1q) with different affinities, resulting in different effector functions. Binding of IgG to the FcγRs or C1q, for example, depends on residues located in the IgG hinge region and CH$_2$ domain. Single or multiple amino acid substitutions of these residues can affect effector function by modulating the IgG interaction with FcγRs or C1q. Other substitutions are known to affect effector function. These modifications are reviewed in Strohl (2009) "Optimization of Fc-mediated effector functions of monoclonal antibodies," *Curr. Opin. Biotechnol.* 20: 685-91, for example.

Representative modifications of the hinge and/or Fc region are summarized in Table 1.

TABLE 1

Representative Hinge and Fc Region Modifications

| Isotype | Species | Substitutions | FcR/C1q Binding | Effector Function | Refs |
|---------|---------|---------------|-----------------|-------------------|------|
| IgG1 | Human | T250Q/M428L | Increased binding to FcRn | Increased half-life | 1 |
| IgG1 | Human | 1M252Y/S254T/T256E + H433K/N434F | Increased binding to FcRn | Increased half-life | 2 |
| IgG1 | Human | E233P/L234V/L235A/G236 + A327G/A330S/P331S | Reduced binding to FcγRI | Reduced ADCC and CDC | 3, 4 |
| IgG1 | Human | E333A | Increased binding to FcγRIIIa | Increased ADCC and CDC | 5, 6 |
| IgG1 | Human | S239D/A330L/I332E | Increased binding to FcγRIIIa | Increased ADCC | 7, 8 |
| IgG1 | Human | P257I/Q311 | Increased binding to FcRn | Unchanged half-life | 9 |

TABLE 1-continued

Representative Hinge and Fc Region Modifications

| Isotype | Species | Substitutions | FcR/C1q Binding | Effector Function | Refs |
|---|---|---|---|---|---|
| IgG1 | Human | K326W/E333S | Increased binding to C1q | Increased CDC | 10 |
| IgG1 | Human | S239D/I332E/ G236A | Increased FcγRIIa/ FcγRIIb ratio | Increased macrophage phagocytosis | 11 |
| IgG1 | Human | K322A | Reduced binding to C1q | Reduced CDC | 5 |
| IgG4 | Human | S228P | — | Reduced Fab-arm exchange | 12 |
| IgG2a | Mouse | L235E + E318A/K320A/ K322A | Reduced binding to FcγRI and C1q | Reduced ADCC and CDC | 10 |

1. Hinton et al. (2004) *J. Biol. Chem.* 279(8): 6213-16.
2. Vaccaro et al (2005) *Nature Biotechnol.* 23(10): 1283-88.
3. Armour et al. (1999) *Eur. J. Immunol.* 29(8): 2613-24.
4. Shields et al. (2001) *J. Biol. Chem.* 276(9): 6591-604.
5. Idusogie et al. (2000) *J. Immunol.* 164(8): 4178-84.
6. Idusogie et al. (2001) *J. Immunol.* 166(4): 2571-75.
7. Lazar et al. (2006) *Proc. Nat'l Acad. Sci. USA* 103(11): 4005-10.
8. Ryan et al. (2007) *Mol. Cancer Ther.* 6: 3009-18.
9. Datta-Mannan et al. (2007) *Drug Metab. Dispos.* 35: 86-94.
10. Steurer et al. (1995) *J. Immunol.* 155(3): 1165-74.
11. Richards et al. (2008) *Mol. Cancer Ther.* 7(8): 2517-27.
12. Labrijn et al. (2009) *Nature Biotechnol.* 27(8): 767-71.

Further, recombinant amino acid modifications can be used to decrease structural homogeneity of the expressed polypeptides. A representative example is Peters et al. (2012) *J. Biol. Chem.* 287(29): 24525-33, which discloses Cys to Ser substitutions in the IgG4 hinge region that reduce the disulfide bond heterogeneity and increase Fab domain thermal stability. Similarly, Zhang et al. (2010) *Anal. Chem.* 82: 1090-99 disclose engineering the IgG2 hinge region to limit disulfide bond scrambling and the formation of structural isomers in therapeutic applications. Amino acid modifications to a CH3 domain also can be used to delete carboxy-terminal Lys residues to decrease the number of charge variants. Amino acid modifications also can be used to improve the pharmacological function of recombinant antibodies or antigen-binding fragments thereof. For example, amino acid modifications can be used to increase complement activation, enhance antibody-dependent cellular cytotoxicity (ADCC) by increasing FcγRIIIA binding or decreasing FcγRIIIB binding, and/or increase serum half-life by increasing FcRn binding. Such amino acid modifications are reviewed in Beck et al. (2010) *Nature* 10: 345-52, for example.

Nucleic Acids and Methods of Making scFv-Fc Dimers

A further aspect of the present invention provides nucleic acids encoding scFv-Fc dimers. The isolated nucleic acid may be a synthetic DNA, a non-naturally occurring mRNA, or a cDNA, for example. Examples include the nucleic acids encoding the VH and VL domains set forth in SEQ ID NOS: 3, 5, 7, and 9 of U.S. Pat. No. 6,492,497. Additional nucleic acids include the sequence set forth in SEQ ID NO: 13 of the present invention, which encodes the diabody-5aa set forth in SEQ ID NO: 14, and the sequence set forth in SEQ ID NO: 15, which encodes the leucine zipper peptide-derived dimer having the amino acid sequence set forth in SEQ ID NO: 16. Additional nucleic acids include the sequence set forth in SEQ ID NO: 17, which encodes CAT191(scFv-Fc), which has the amino acid sequence set forth in SEQ ID NO: 9. The nucleic acid may be inserted within a plasmid, vector, or transcription or expression cassette. The nucleic acids encoding the scFv-Fc dimers may be made and the expressed antibodies may be tested using conventional techniques well known in the art, such as disclosed in Borsi et al. (2002) *Int. J. Cancer* 102: 75-85.

A recombinant host cell may comprise one or more constructs above. Methods of preparing scFv-Fc dimers comprise expressing the encoding nucleic acid in a host cell under conditions to produce the scFv-Fc dimers, and recovering the antibodies. The process of recovering the antibodies may comprise isolation and/or purification of the antibodies. The method of production may comprise formulating the antibodies into a composition including at least one additional component, such as a pharmaceutically acceptable excipient.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred enkaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Suitable vectors comprising a nucleic acid encoding scFv-Fc dimers can be chosen or constructed, containing appropriate regulatory sequences, including promoter sequences, terminator sequences, polyadenylation sequences, enhancer sequences, marker genes and other sequences as appropriate. Vectors may be plasmids, phage, phagemids, adenoviral, AAV, lentiviral, for example. Techniques and protocols for manipulation of nucleic acid, for example in preparation of nucleic acid constructs, mutagenesis, sequencing, introduction of DNA into cells, and gene expression, are well known in the art.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adena-associated viruses), which serve equivalent functions.

Introducing such nucleic acids into a host cell can be accomplished using techniques well known in the art. For eukaryotic cells, suitable techniques may include calcium phosphate transfection, DEAE-Dextran, electroporation, liposome-mediated transfection, and transduction using retroviruses or other viruses, for example. For bacterial cells, suitable techniques may include calcium chloride transformation, electroporation, and transfection using bacteriophage. The introduction may be followed by causing or allowing expression from the nucleic acid, e.g. by culturing host cells under conditions for expression of the gene. In one embodiment, the nucleic acid of the invention is integrated into the genome, e.g., chromosome, of the host cell. Integration may be promoted by inclusion of sequences which promote recombination with the genome, in accordance with standard techniques.

Systems for cloning and expression of a polypeptide in a variety of different host cells are well known. Suitable host cells include bacteria, mammalian cells, plant cells, insect cells, fungi, yeast and transgenic plants and animals. Mammalian cell lines available in the art for expression of a heterologous polypeptide include Chinese hamster ovary (CHO) cells, HeLa cells, baby hamster kidney cells, mouse melanoma cells, rat myeloma cells, human embryonic kidney cells, e.g., HEK293 cells, human embryonic retina cells, and many others. The expression of antibodies and antibody fragments in prokaryotic cells, such as E. coli, is well established in the art. For a review, see for example, Plückthun Bio/Technology 9: 545-551 (1991). Expression in cultured eukaryotic cells is also available to those skilled in the art, as reviewed in Andersen et al. (2002) Curr. Opin. Biotechnol. 13: 117-23, for example.

scFv-Fc dimers may be glycosylated, either naturally or the choice of expression host, e.g., CHO, HEK293, or NSO (ECACC 85110503) cells, or they may be unglycosylated, for example if produced by expression in a prokaryotic cell. Glycosylation may also be intentionally altered, for example by inhibiting fucosylation, in order to increase ADCC activity of the resulting scFv-Fc dimer.

Methods of Using Antibodies or Antigen-Binding Fragments Thereof

The scFv-Fc dimers may be used in a method of treatment or diagnosis of the human or animal body, such as a method of treatment (which may include prophylactic treatment) of a disease or disorder in a human patient, which comprises administering an effective amount to treat the patient. Treatable conditions include any in which TGFβ1 plays a role, e.g., a fibrotic disease, cancer, an immune-mediated disease, and wound healing, e.g., diffuse systemic sclerosis, bone remodeling disease, kidney disease and/or combinations thereof.

Antibodies specific for human TGFβ1 have been shown to be effective in animal models for the treatment of TGFβ1 glomerulonephritis (Border et al. (1990) Nature 346: 371-374), neural scarring (Logan et al. (1994) Eur. J. Neurosci. 6: 355-363), dermal scarring (Shah et al. (1992) Lancet 339: 213-214; Shah et al. (1994) J. Cell Science 107: 1137-1157; Shah et al. (1995) J. Cell Science 108: 985-1002), and pulmonary fibrosis (Giri et al. (1993) Thorax 48: 959-966). Further, antibodies to TGFβ1, 2, and 3 have been shown to be effective in models of lung fibrosis, radiation induced fibrosis (U.S. Pat. No. 5,616,561), myelofibrosis, burns, Dupuytren's contracture, gastric ulcers, and rheumatoid arthritis (Wahl et al. (1993) Exp. Medicine 177: 225-230).

The scFv-Fc dimers are useful to treat a disease and condition resulting directly or indirectly from TGFβ1 activity. The scFv-Fc dimers may selectively inhibit the activity of a human TGFβ1 isoform in vitro or in vivo. Activities of TGFβ1 isoforms include, but are not limited to, TGFβ-mediated signaling, extracellular matrix (ECM) deposition, inhibiting epithelial and endothelial cell proliferation, promoting smooth muscle proliferation, inducing Type III collagen expression, inducing TGF-β, fibronectin, VEGF, and IL-11 expression, binding Latency Associated Peptide, tumor-induced immunosuppression, promotion of angiogenesis, activating myofibroblasts, promotion of metastasis, and inhibition of NK cell activity. For example, the scFv-Fc dimers are useful to treat focal segmental glomerulosclerosis (FSGS), hepatic fibrosis (HF), acute myocardial infarction (AMI), idiopathic pulmonary fibrosis (IPF), scleroderma (SSc), and Marfan Syndrome.

The scFv-Fc dimers are useful to treat diseases and conditions including, but not limited to, a fibrotic diseases (such as glomerulonephritis, neural scarring, dermal scarring, pulmonary fibrosis, lung fibrosis, radiation induced fibrosis, hepatic fibrosis, myelofibrosis), burns, immune mediated diseases, inflammatory diseases (including rheumatoid arthritis), transplant rejection, cancer, Dupuytren's contracture, and gastric ulcers. They are also useful for treating, preventing and reducing the risk of occurrence of renal insufficiencies including but not limited to: diabetic (type I and type II) nephropathy, radiation-induced nephropathy, obstructive nephropathy, diffuse systemic sclerosis, pulmonary fibrosis, allograft rejection, hereditary renal disease (e.g., polycystic kidney disease, medullary sponge kidney, horseshoe kidney), glomerulonephritis, nephrosclerosis, nephrocalcinosis, systemic lupus erythematosus, Sjogren's syndrome, Berger's disease, systemic or glomerular hypertension, tubulointerstitial nephropathy, renal tubular acidosis, renal tuberculosis, and renal infarction. In particular, they are useful when combined with antagonists of the renin-angiotensin-aldosterone system including, but not limited to: renin inhibitors, angiotensin-converting enzyme (ACE) inhibitors, Ang II receptor antagonists (also known as "Ang II receptor blockers"), and aldosterone antagonists. Methods for using scFv-Fc dimers in combination with such antagonists are set forth in WO 2004/098637, for example.

The scFv-Fc dimers also are useful to treat diseases and conditions associated with the deposition of ECM, including, systemic sclerosis, postoperative adhesions, keloid and hypertrophic scarring, proliferative vitreoretinopathy, glaucoma drainage surgery, corneal injury, cataract, Peyronie's disease, adult respiratory distress syndrome, cirrhosis of the liver, post myocardial infarction scarring, post angioplasty restenosis, scarring after subarachnoid hemorrhage, multiple sclerosis, fibrosis after laminectomy, fibrosis after tendon and other repairs, scarring due to tattoo removal, biliary cirrhosis (including sclerosing cholangitis), pericarditis, pleurisy, tracheostomy, penetrating central nervous system injury, eosinophilic myalgic syndrome, vascular restenosis, veno-occlusive disease, pancreatitis and psoriatic arthropathy.

The scFv-Fc dimers further are useful to promote re-epithelialization in diseases and conditions such as venous ulcers, ischaemic ulcers (pressure sores), diabetic ulcers, graft sites, graft donor sites, abrasions and burns, diseases of the bronchial epithelium, such as asthma, ARDS, diseases of the intestinal epithelium, such as mucositis associated with cytotoxic treatment, esophageal ulcers (reflux disease), stomach ulcers, small intestinal and large intestinal lesions (inflammatory bowel disease).

The scFv-Fc dimers also may be used to promote endothelial cell proliferation, for example, in stabilizing atherosclerotic plaques, promoting healing of vascular anastomoses, or to inhibit smooth muscle cell proliferation, such as in arterial disease, restenosis and asthma.

The scFv-Fc dimers are useful to enhance the immune response to macrophage-mediated infections. They are also useful to reduce immunosuppression caused, for example, by tumors, AIDS, or granulomatous diseases. The scFv-Fc dimers are useful to treat hyperproliferative diseases, such as cancers including, but not limited to, breast, prostate, ovarian, stomach, renal, pancreatic, colorectal, skin, lung, cervical and bladder cancers, glioma, mesothelioma, as well as various leukemias and sarcomas, such as Kaposi's sarcoma, and are useful to treat or prevent recurrences or metastases of such tumors. The scFv-Fc dimers of the invention also are useful to inhibit cyclosporin-mediated metastases.

In the context of cancer therapy, "treatment" includes any medical intervention resulting in the slowing of tumor growth or reduction in tumor metastases, as well as partial remission of the cancer in order to prolong life expectancy of a patient.

Methods of treatment comprise administering a scFv-Fc dimer or pharmaceutical compositions comprising the scFv-Fc dimer. The scFv-Fc dimers may be used in the manufacture of a medicament for administration. For example, a method of making a medicament or pharmaceutical composition comprises formulating a scFv-Fc dimer with a pharmaceutically acceptable excipient. A composition may be administered alone or in combination with other treatments, either simultaneously or sequentially dependent upon the condition to be treated.

Administration is preferably in a "therapeutically effective amount" sufficient to show benefit to a patient. Such benefit may be at least amelioration of at least one symptom of a particular disease or condition. The actual amount administered, and rate and time-course of administration, will depend on the nature and severity of the disease or condition being treated. Prescription of treatment, e.g., decisions on dosage etc., may be determined based on preclinical and clinical studies the design of which is well within the level of skill in the art.

The precise dose will depend upon a number of factors, including whether the scFv-Fc dimer is for diagnosis or for treatment, the size and location of the area to be treated, and the nature of any detectable label or other molecule attached to the scFv-Fc dimer. A typical dose of a scFv-Fc dimer, for example, can be in the range 100 µg to 1 gram for systemic applications, and 1 µg to 1 mg for topical applications. The dose for a single treatment of an adult patient may be adjusted proportionally for children and infants. Treatments may be repeated at daily, twice-weekly, weekly, monthly or other intervals, at the discretion of the physician. Treatment may be periodic, and the period between administrations is about two weeks or more, preferably about three weeks or more, more preferably about four weeks or more, or about once a month.

Dose levels of about 0.1, 0.3, 1, 3, 10, or 15 mg per kg body weight of the 15 patient are expected to be useful and safe. For example, 0.5-5 mg/kg in rat and mouse has been an effective dose in an acute setting. Therefore, for long-term dosing, 0.3-10 mg/kg may be administered to humans, based on an expected half-life of 21 days. Doses may be sufficient for efficacy, while low enough to facilitate optimal administration. For example, a dose of less than 50 mg facilitates subcutaneous administration. Intravenous administration may be used as the route of delivery for severe diseases, where high doses and the long dosing intervals may be required. Subcutaneous injection can increase the potential immune response to a product. Local administration for localized disease can reduce the amount of administered product and increase the concentration at the site of action, which can improve safety.

The scFv-Fc dimers of the invention may be administered by injection, for example, subcutaneously, intravenously, intracavity (e.g., after tumor resection), intralesionally, intraperitoneally, or intramuscularly. ScFv-Fc dimers also may be delivered by inhalation or topically (e.g., intraocular, intranasal, rectal, into wounds, on skin), or orally.

A scFv-Fc dimer will usually be administered in the form of a pharmaceutical composition, which may comprise at least one component in addition to the scFv-Fc dimer. Thus pharmaceutical compositions may comprise a pharmaceutically acceptable excipient, carrier, buffer, stabilizer or other materials well known to those skilled in the art. Such materials should be non-toxic and should not interfere with the efficacy of the active ingredient. Such materials could include, for example, any and all solvents, dispersion media, coatings, antibacterial and antifungal agents, isotonic, and absorption delaying agents. Some examples of pharmaceutically acceptable carriers are water, saline, phosphate buffered saline, dextrose, glycerol, ethanol, and the like, as well as combinations thereof. In many cases, it will be preferable to include isotonic agents, for example, sugars, polyalcohols, such as mannitol, sorbitol, or sodium chloride in the composition. Additional examples of pharmaceutically acceptable substances are wetting agents or auxiliary substances, such as emulsifying agents, preservatives, or buffers, which increase the shelf life or effectiveness.

The precise nature of the carrier or other material will depend on the route of administration. For intravenous injection, or injection at the site of affliction, the active ingredient will be in the form of a parenterally acceptable aqueous solution which is pyrogen-free and has suitable pK, isotonicity, and stability. Those of relevant skill in the art are well able to prepare suitable solutions using, for example, isotonic vehicles such as sodium chloride injection, Ringer's injection, and lactated Ringer's injection. Preservatives, stabilizers, buffers, antioxidants, and/or other additives may be included.

A scFv-Fc dimer may be formulated in liquid, semi-solid, or solid forms, such as liquid solutions (e.g., injectable and infusible solutions), dispersions or suspensions, powders, liposomes, and suppositories. The preferred form depends on the intended mode of administration, the therapeutic application, the physicochemical properties of the molecule, and the route of delivery. Formulations may include excipients, or combinations of excipients, for example: sugars, amino acids and surfactants. Liquid formulations may include a wide range of scFv-Fc dimer concentrations and pH. Solid formulations may be produced by lyophilization, spray drying, or drying by supercritical fluid technology, for example.

Therapeutic compositions can be formulated as a solution, microemulsion, dispersion, liposome, or other ordered structure suitable to high drug concentration. Sterile injectable solutions can be prepared by incorporating the scFv-Fc dimer in an appropriate solvent with one or a combination of ingredients enumerated above, followed by filtered sterilization. Generally, dispersions are prepared by incorporating the active compound into a sterile vehicle that contains a basic dispersion medium and other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by using a coating such as lecithin, by maintaining the particle size of a dispersion, or by using surfactants. Prolonged absorption of injectable compositions can be brought about by including in the composition an agent that delays absorption, for example, monostearate salts and gelatin.

In certain embodiments, the active compound may be prepared with a carrier that will protect the scFv-Fc dimer against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art.

A method of using a scFv-Fc dimer may comprise causing or allowing binding to TGFβ. Such binding may take place in vivo, e.g., following administration of a scFv-Fc dimer to a patient, or it may take place in vitro, e.g., in ELISA, Western blotting, immunocytochemistry, immunoprecipitation, affinity chromatography, or cell based assays, or in ex vivo based therapeutic methods, e.g., methods in which cells or bodily fluids are contacted ex vivo with a scFv-Fc dimer and then administered to a patient.

A kit comprising a scFv-Fc dimer is provided. The scFv-Fc dimer may be labeled to allow its reactivity in a sample to be determined. Kits may be employed in diagnostic analysis, for example. A kit may contain instructions for use of the components. Ancillary materials to assist in or to enable performing such a method may be included within the kit.

The reactivity of a scFv-Fc dimer in a sample may be determined by any appropriate means, e.g., radioimmunoassay (RIA). Radioactively labeled antigen may be mixed with unlabeled antigen (the test sample) and allowed to bind to the scFv-Fc dimer. Bound antigen is physically separated from unbound antigen and the amount of radioactive antigen bound to the scFv-Fc dimer is determined. A competitive binding assay also may be used with non-radioactive antigen, using an antigen or an analogue linked to a reporter molecule. The reporter molecule may be a fluorochrome, phosphor, or dye. Suitable fluorochromes include fluorescein, rhodamine, phycoerythrin and Texas Red Suitable chromogenic dyes include diaminobenzidine.

Other reporters include macromolecular colloidal particles or particulate material such as latex beads that are colored, magnetic or paramagnetic, and biologically or chemically active agents that can directly or indirectly cause detectable signals to be visually observed, electronically detected or otherwise recorded These molecules may be enzymes that catalyze reactions that develop or change colors or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. The signals generated by antibody-reporter conjugates may be used to derive quantifiable absolute or relative data of the relevant antibody binding in samples.

The present invention also provides the use of a scFv-Fc dimer for measuring antigen levels in a competition assay. The scFv-Fc dimer can be linked to a reporter molecule so that a physical or optical change occurs on binding, for example. The reporter molecule may directly or indirectly generate detectable, and preferably measurable, signals. The reporter molecules may be linked directly or indirectly, covalently, e.g., via a peptide bond or non-covalently. The scFv-Fc dimer and a protein reporter may be linked by a peptide bond and recombinantly expressed as a fusion protein.

Further aspects and embodiments of the present invention will be apparent to those skilled in the art in the light of the present disclosure, including the following experimental exemplification.

EXAMPLES

Example 1

Affinity and Potency of scFv and IgG4 Antibody

Figure 2:
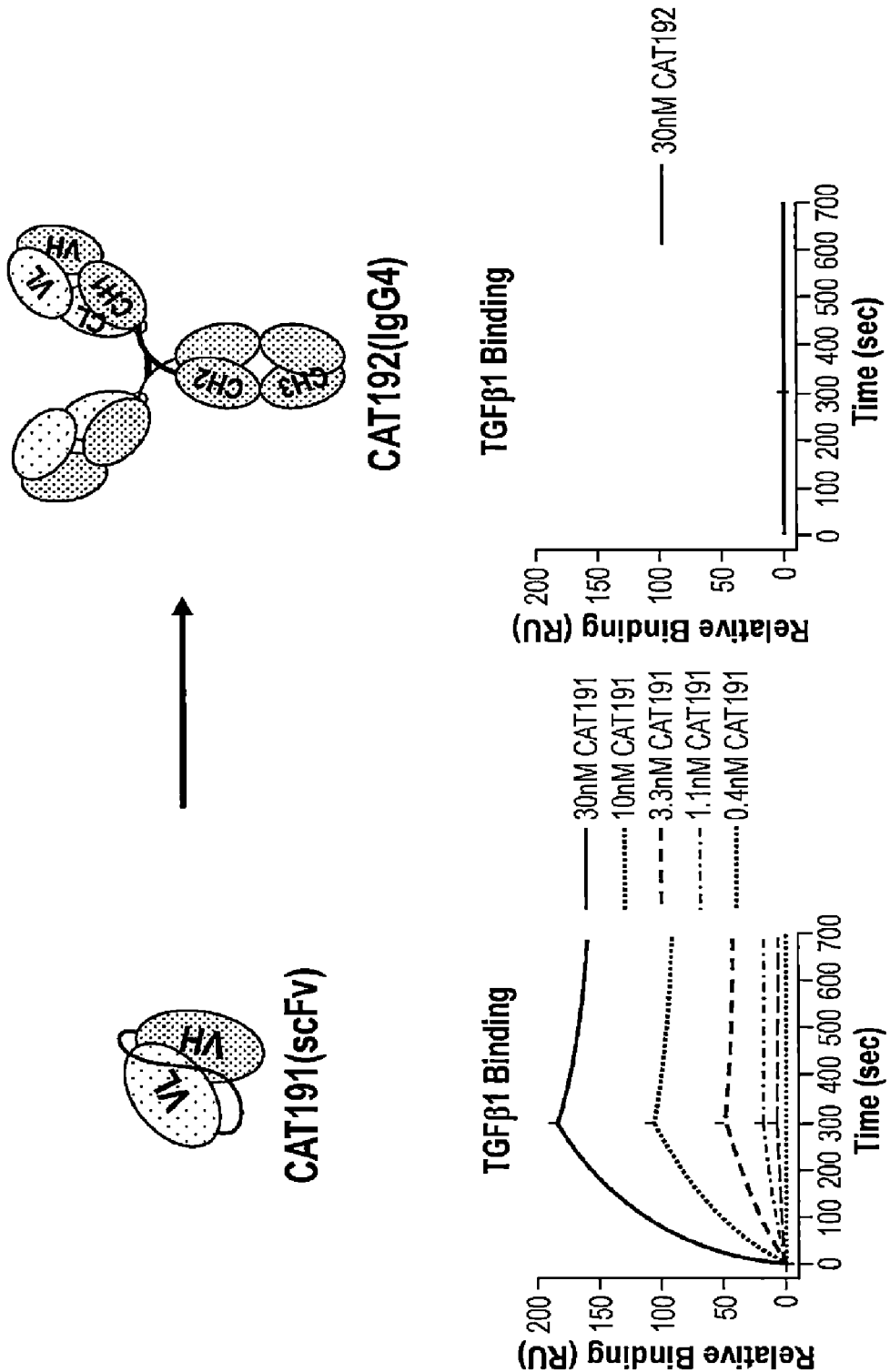
FIG. 2 depicts the results of a Biacore TGF1 binding assay which showed the loss of affinity when the scFv(CAT191) was converted into a full length IgG4 (CAT192) molecule.

CAT192(IgG4) (metelimumab) is a human IgG4 monoclonal antibody that selectively neutralizes TGF-β1. TGFβ1 (20-600RU) was immobilized to a CM5 chip on Biacore using NHS/EDC chemistry. Various amounts of CAT192 (IgG4) were injected over the surface to monitor the binding to TGβ1 determined by surface plasmon resonance. The data were analyzed with a 1:1 binding model to determine binding constants. CAT192(IgG4) was found to bind TGFβ1 with relatively low affinity as determined by surface plasmon resonance, when compared to the binding by the parental CAT191scFv as shown in FIG. 2. CAT192(IgG4) also showed a relatively low efficacy (IC50=~10 nM) in an A549 cell-based potency assay, which measured inhibition of TGFβ1-stimulated IL-11 production. Representative results of an A549 assay are shown in FIG. 3. The A549 assay was conducted according to the procedure disclosed in Rapoza et al. (2006) "Development of an in vitro potency assay for therapeutic TGFβ antagonists: the A549 cell bioassay," *J. Immunol. Methods* 316: 18-26. While an apparent dissociation constant of ~10 nM showed specific binding to TGFβ1, therapeutic applications of CAT192 (IgG4) would benefit from a higher relative potency.

Example 2

Modified IgG1 Antibody

CAT192(IgG4) affinity can be slightly enhanced by certain denaturing conditions, suggesting that antibody folding may have caused the loss of affinity during the conversion of scFv to IgG4. IgG4 folding has been proposed to be unique (Aalberse and Schuurman "IgG4 breaking the rules", Immunology 105:9-19). The Fab arm exchange in IgG4 and the interaction of Fabs with Fc CH2 domain may possibly explain this loss of affinity by CAT192(IgG4). Therefore, CAT192 was remodeled to produce the IgG1 version by replacing IgG4 Fc (CH1, CH2 and CH3 domains) with the consensus IgG1 sequence. The DNA coding the CAT192 (IgG1) was synthesized from GeneArt and subcloned into expression vector pCEP4(-E+I)Dest.

CAT192(IgG1) was produced from HEK293 transfection and purified with Protein A column. Remodeling CAT192 from IgG4 to IgG1, however, did not increase its affinity. Fab fragments generated from the IgG1 and IgG4 did not increase its affinity either. It was concluded that the high affinity of CAT191(scFv) (SEQ ID NO: 12) was lost during conversion to a full-length antibody format, whether it was a IgG1 or IgG4. This was unexpected, because scFv components obtained from a library are often engineered to a full-length IgG format for therapeutic development.

Example 3

Various Dimer Designs

Figure 1:
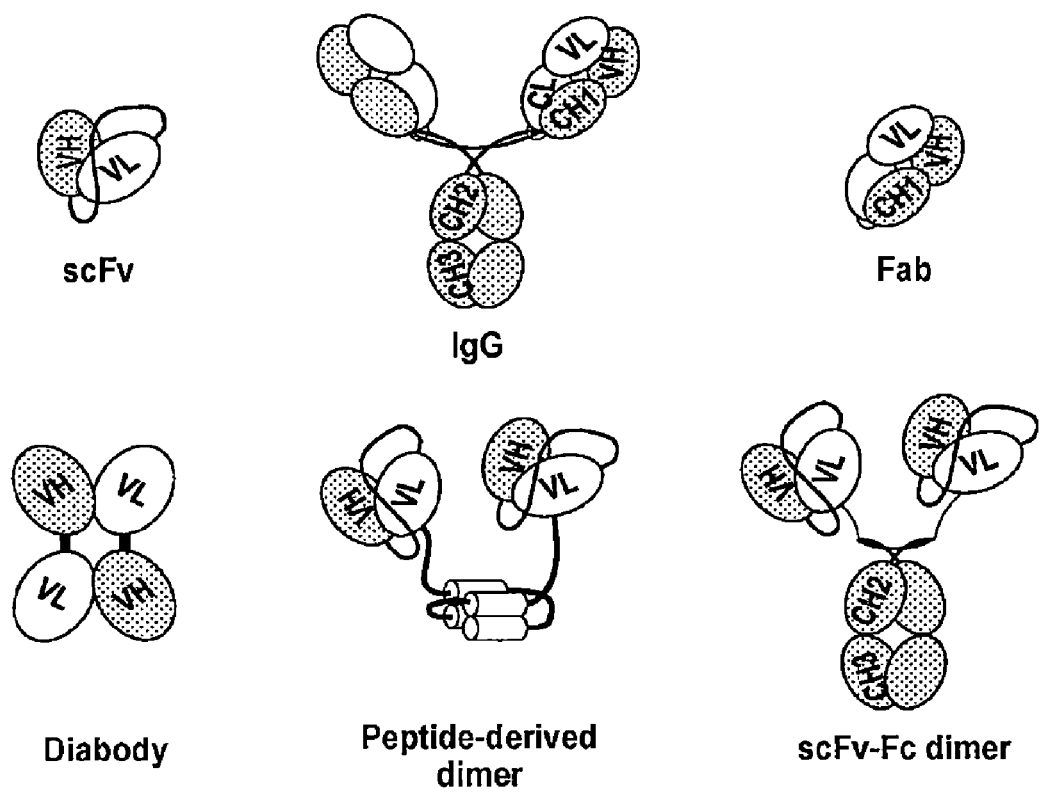
FIG. 1 depicts the general structures of the various formats.

CAT191(scFv) (SEQ ID NO: 12) was found to bind TGFβ1 with high affinity, using surface plasmon resonance, but CAT191(scFv) lacked the avidity needed for effective neutralization of TGFβ1. Accordingly, various other formats were tested, using the scFv component as a basic building block General formats of antibody fragments, including the tested formats, are depicted in FIG. 1.

Tested formats included a diabody, a peptide-derived dimer (e.g., a leucine zipper peptide-derived dimer), and an scFv-Fc dimer. scFv CAT191 diabody had the (Gly4Ser)3-type linker replaced with a short 5aa linker (GSSGG) (SEQ ID NO: 19) to create a non-covalent divalent binder (diabody dimer). Each monomer had the sequence set forth in SEQ ID NO: 14. Each monomer of the leucine zipper peptide-derived dimer had the sequence set forth in SEQ ID NO: 16. Finally, each monomer of the scFv-Fc dimer had the sequence set forth in SEQ ID NO: 9. The diabody and the peptide derived dimer were expressed in *E. Coli* and the scFv-Fc was expressed in HEK293 cells.

The leucine zipper peptide-derived dimer was difficult to express, and the partially purified dimer only showed intermediate affinity, as measured by surface plasmon resonance. The diabody (scFv 5aa) only showed intermediate affinity, but no avidity. By contrast, a scFv-Fc dimer produced from transient HEK293 transfection was found to bind to TGFβ1 specifically with high affinity and avidity. The binding results expressed as apparent dissociation constants obtained with surface plasmon resonance are summarized below in Table 2.

TABLE 2

Binding Results for scFv-Fc Dimer

| Sample | 24 RU TGFβ1 $K_D$ (nM) | 105 RU TGFβ1 $K_D$ (nM) | 544 HU TGFβ1 $K_D$ (nM) | |
|---|---|---|---|---|
| scFv-Fc | 0.5 | 0.2 | 0.09 | Avidity |
| CAT191 scFv | 1.7 | 1.6 | 1.3 | No |
| scFv 5aa | 4.1 | 3.0 | 4.8 | Avidity |

The TGFβ1 neutralizing potency of various formats was also compared in the A549 cell-based bioassay. FIG. 3 shows the A549 bioassay results for the diabody ("scFv diabody 5aa"), CAT191(scFv) ("scFv"), the scFv-Fc dimer ("CAT191(scFv-Fc)"), and CAT192(IgG4) ("CAT192"). As seen in FIG. 3, the scFv-Fc dimer demonstrated an apparent dissociation constant in this assay over four orders of magnitude lower than CAT192 (~$10^{-3}$ nM versus ~$10^{-1}$ nM).

Example 4 scFv-Fc Clone

CAT191(scFv-Fc) was cloned and produced in larger scale in CHO cells. CAT191 scFv-Fc coding sequence was PCR amplified from a pCEP4 based expression vector using a gene specific forward and reverse primer set. As part of the PCR amplification the following changes were introduced to the CAT191 scFv-Fc coding sequence: 1) addition of endonuclease sites at the 5' and 3' ends, 2) addition of Kozak consensus sequence immediately upstream of the start codon, 3) change of the "TAG" stop codon to "TAA", and 4) mutation of the thymidine 4 nucleotides upstream of the stop codon to a guanosine thus eliminating an endogenous splice donor site. The splice donor site mutation did not result in an amino acid change.

The PCR amplified CAT191 coding sequence was subcloned into a shuttle vector to facilitate sequence verification and molecular cloning. After sequence verification, the CAT191 coding sequence was cloned into Genzyme expression vectors pGZ600 and pGZ620. Both vectors used the hamster β-actin promoter to drive expression of the CAT191 transgene. They also contained the DHFR selectable marker that was driven by a separate promoter (SV40) to enable selection in CHO cells. CHO-8D6 host cell line was transfected with either the pGZ600-CAT191 or pGZ620-CAT191 expression plasmid. Following a brief recovery period, the transfected cells were placed into nucleotide-deficient growth medium for selection to generate pools of stable transfectants. After pools recovered from selection, a second round of selection was performed in the presence of 20 nM methotrexate. The CHO pools selected this way was scaled up and the conditioned media was used for purification using Protein A column.

The CHO cell-produced protein was characterized by SDS-PAGE, Biacore binding, SEC-HPLC, and the A549 cell potency assay. The results confirmed that the scFv-Fc dimer had a higher affinity and potency, and it specifically neutralized TGFβ1. The potency compared favorably to the pan-specific GC1008 antibody (FIG. 6 and FIG. 7).

Example 5

Circulation Half-Life

The circulation half-life of CAT191(scFv-Fc) was tested in a mouse model using the study design depicted in Table 3.

TABLE 3

Circulation Half-Life of scFv-Fc Dimer

| Group | Animal #'s | Test Article | Dose (mg/kg) | Dose Route | Time Points |
|---|---|---|---|---|---|
| 1 | 1-6 | scFv-Fc | 1.0 | IP | 2, 6, 24, 72, 144, 240, and 336 hours post-dose |
| 2 | 9-16 | scFv-Fc | 1.0 | IV | 0.25, 6, 24, 72, 144, 240, and 336 hours post-dose |

Blood was drawn from the retro-orbital plexus at the specified times after intraperitoneal (IP) or intravenous (IV) administration. Approximately 60 μL of whole blood was collected into hematocrit tubes and processed for serum. All samples was stored at −80° C. until analysis. The CAT191

(scFv-Fc) concentration was determined by ELISA. The results of this pharmacokinetic study are depicted in FIG. 4 and FIG. 5. The results suggested a circulation half-life of 1.5-2.0 days, much longer than that for a typical scFv molecule, which is several hours.

Example 6 scFv-Fc Dimer Stability

The stability of CAT191(scFv-Fc) stored at −80° C. was monitored for a year by SEC-HPLC, Biacore TGFβ1 binding, and the A549 potency assay. No change in aggregation, affinity, or potency was observed during the test period. Material stored at 4° C. displayd a slight but steady increase in aggregation over 1 year. The unique combination of the smaller size, high selectivity, potency against TGFβ1, and long in vivo half-life made CAT191(scFv-Fc) an ideal candidate for therapeutic applications.

All documents cited throughout this disclosure, including but not limited to scientific publications, patents and publication of patent applications, are hereby incorporated by reference in this disclosure as if the full contents are reproduced herein.

```
                           SEQUENCE LISTING

SEQ ID No. 1: Human IgG1 VH domain Clone SL15 (SQN4 U.S. Pat. No. 6492497)
EVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSS SEQ ID No. 2: Human IgG1 VH domain Clone JT182 (SQN10 U.S. Pat. No. 6492497)
QVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTPASPDWGQGTTVTVSS SEQ ID No. 3: Synthetic linker
SGGGSGGGGSGGGGS SEQ ID No. 4: Synthetic linker
GGGGSGGGGSGGGGS SEQ ID No. 5: Human IgG1 Vκ domain Clone SL15A: (SQN6 U.S. Pat. No. 6492497)
EIVLTQSPSSLSASVGDRVTITCRASQGIGDDLGWYQQKPGKAPILLIYGTSTL
QSGVPSRFSGSGSGTDFTLTINSLQPEDFATYYCLQDSNYPLTFGGGTRLEIK SEQ ID No. 6: Human IgG1 Vκ domain Clone SL15S: (SQN8 U.S. Pat. No. 6492497)
EIVLTQSPSSLSASVGDRVTITCRSSQGIGDDLGWYQQKPGKAPILLIYGTSTL
QSGVPSRFSGSGSGTDFTLTINSLQPEDFATYYCLQDSNYPLTFGGGTRLEIK SEQ ID No. 7: Human IgG1 hinge region
PKSCDKTHTCPPCPAPELLGGP SEQ ID No. 8: Human IgG1 Fc region
SVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQ
PREPQVYTLPPSRDELTKNQVSLTCLVKGFYPSDIAVEWESNGQPENNYKTTP
PVLDSDGSFFLYSKLTVDKSRWQQGNVFSCSVMHEALHNHYTQKSLSLSPGK SEQ ID No. 9: CAT191(scFv-Fc)
EVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSSSGGGSGGGGSGGGGSEIVLTQSPSSLSASVGD
RVTITCRSSQGIGDDLGWYQQKPGKAPILLIYGTSTLQSGVPSRFSGSGSGTDF
TLTINSLQPEDFATYYCLQDSNYPLTFGGGTRLEIKGGSGPKSCDKTHTCPPCP
APELLGGPSVFLFPPKPKDTLMISRTPEVTCVVVDVSHEDPEVKFNWYVDGV
EVHNAKTICPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYT
QKSLSLSPGK SEQ ID No. 10: CAT192 (IgG4) Light Chain
EWLTQSPSSLSASVGDRVTITCRASQGIGDDLGWYQQKPGKAPILLIYGTSTL
QSGVPSRFSGSGSGTDFTLTINSLQPEDFATYYCLQDSNYPLTFGGGTRLEIKR
TVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGE
C SEQ ID No. 11: CAT192 (IgG4) Heavy Chain
EVQLVESGGGVVQPGRSLRLSCAASGFFFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSSASTKGPSVFPLAPCSRSTSESTAALGCLVKDYF
PEPVTVSWNSGALTSGVHTFPAVLQSSGLYSLSSVVTVPSSSLGTKTYTCNVD
HKPSNTKVDKRVESKYGPPCPSCPAPEFLGGPSVFLFPPKPKDTLMISRTPEVT
CVVVDVSQEDPEVQFNWYVDGVEVHNAKTKPREEQFNSTYRVVSVLTVLHQ
DWLNGKEYKCKVSNKGLPSSIEKTISKAKGQPREPQVYTLPPSQEEMTKNQV
SLTCLVKGFYPSDIAVEWESNGQPENNYKTTPPVLDSDGSFFLYSRLTVDKSR
WQEGNVFSCSVMHEALHNHYTQKSLSLSLGK
```

SEQUENCE LISTING

SEQ ID No. 12: CAT191(scFv)
EVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSSSGGGSGGGGSGGGGSEIVLTQSPSSLSASVGD
RVTITCRSSQGIGDDLGWYQQKPGKAPILLIYGTSTLQSGVPSRFSGSGSGTDF
TLTINSLQPEDFATYYCLQDSNYPLTFGGGTRLEIK

SEQ ID No. 13: Diabody-5 aa encoding nucleic acid
atgaccatgattacgccaagctttggagccttttttttggagattttcaacgtgaaaaaattattattcgcaattcctttagttgttcc
tttctatgcggcccagccggccatggccgaggtgcagctggtggagtctggggggaggcgtggtccagcctggggaggtcc
ctgagactctcctgtgcagcctctggattcaccttcagtagctatggcatgcactgggtccgccaggctccaggcaaggag
ctggagtgggtggcagttatatcatatgatggaagtattaaatactatgcagactccgtgaagggccgattcaccatctccag
agacaattccaagaacacgctgtatctgcaaatgaacagcctgagagctgaggacacggctgtgtattactgtgcgcgaac
tggtgaatatagtggctacgatacggaccccccagtactcctgggggcaagggaccacggtcaccgtctcctcaggttcctc
tggcggtgaaattgtgctgactcagtctccatcctccctgtctgcatctgtaggagacagagtcaccatcacttgccggtcaa
gtcagggcattggagatgatttgggaggtatcagcagaagccagggaaagcccctatcctcctgatctatggtacatccac
tttacaaagtggggtcccgtcaaggttcagcggcagtggatctggcacagatttcactctcaccatcaacagcctgcagcct
gaagattttgcaacttattactgtctacaagattccaattacccgctcactacggcggagggacacgactggagattaaacgt
gcggccgcacatcatcatcaccatcacggggccgcagaacaaaaactcatctcagaagaggatctgaatgggccgcat
agtagctcgagatcaaacgggctagccagccagaactcgccccgaagaccccgaggatgtcgagcaccaccaccac
ac SEQ ID No. 14: Diabody-5 aa
EVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSSGSSGGEIVLTQSPSSLSASVGDRVTITCRSSQGI
GDDLGWYQQKPGKAPILLIYGTSTLQSGVPSRFSGSGSGTDFTLTINSLQPEDF
ATYYCLQDSNYPLTFGGGTRLEIKRAAAHHHHHHGAAEQKLISEEDLNGAA SEQ ID No. 15: Leucine zipper peptide-derived dimer encoding nucleic acid
gaggtgcagctggtggagtctggggggaggcgtggtccagcctggggaggtccctgagactctcctgtgcagcctctggatt
caccttcagtagctatggcatgcactgggtccgccaggctccaggcaaggagctggagtgggtggcagttatatcatatga
tggaagtattaaatactatgcagactccgtgaagggccgattcaccatctccagagacaattccaagaacacgctgtatctg
caaatgaacagcctgagagctgaggacacggctgtgtattactgtgcgcgaactggtgaatatagtggctacgatacggac
cccagtactcctgggggcaagggaccacggtcaccgtctcctcaagtggaggcggttcaggcggaggtggcagcggc
ggtggcggatcggaaattgtgctgactcagtctccatcctccctgtctgcatctgtaggagacagagtcaccatcacttgccg
gtcaagtcagggcattggagatgatttgggctggtatcagcagaagccagggaaagcccctatcctcctgatctatggtaca
tccactttacaaagtggggtcccgtcaaggttcagcggcagtggatctggcacagatttcactctcaccatcaacagcctgc
agcctgaagattagcaacttattactgtctacaagattccaattacccgctcactttcggcggagggacacgactggagatta
aacgtgcggccgcacatcatcatcaccatcacggggccgcagaacaaaaactcatctcagaagaggatctgaatgggc
cgcacccaagcccagtaccccccaggttcttcaggcgaactggaagaactgctgaaacatctgaaagaactgctgaaag
gcccgcgtaaaggcgaactggaagaactgctgaaacatctgaaagaactgagaaaggcggtgcgccgggcggtcatc
atcatcaccatcat SEQ ID No. 16: Leucine zipper peptide-derived dimer
EVQLVESGGGVVQPGRSLRLSCAASGFTFSSYGMHWVRQAPGKELEWVAVI
SYDGSIKYYADSVKGRFTISRDNSKNTLYLQMNSLRAEDTAVYYCARTGEYS
GYDTDPQYSWGQGTTVTVSSSGGGSGGGGSGGGGSEIVLTQSPSSLSASVGD
RVTITCRSSQGIGDDLGWYQQKPGKAPILLIYGTSTLQSGVPSRFSGSGSGTDF
TLTINSLQPEDFATYYCLQDSNYPLTFGGGTRLEIKRAAAHHHHHHGAAEQK
LISEEDLNGAAPKPSTPPGSSGELEELLKHLKELLKGPRKGELEELLKHLKELL
KGGAPGGHHHHHH SEQ ID No. 17: CAT191(scFv-Fc) encoding nucleic acid
gaggtgcagctggtggagtctggggggaggcgtggtccagcctggggaggtccctgagactctcctgtgcagcctctggatt
caccttcagtagctatggcatgcactgggtccgccaggctccaggcaaggagctggagtgggtggcagttatatcatatga
tggaagtattaaatactatgcagactccgtgaagggccgattcaccatctccagagacaattccaagaacacgctgtatctg
caaatgaacagcctgagagctgaggacacggctgtgtattactgtgcgcgaactggtgaatatagtggctacgatacggac
cccagtactcctgggggcaagggaccacggtcaccgtctcctcaagtggaggcggttcaggcggaggtggcagcggc
ggtggcggatcggaaattgtgctgactcagtctccatcctccctgtctgcatctgtaggagacagagtcaccatcacttgccg
gtcaagtcagggcattggagatgatttgggctggtatcagcagaagccagggaaagcccctatcctcctgatctatggtaca
tccactttacaaagtggggtcccgtcaaggttcagcggcagtggatctggcacagatttcactctcaccatcaacagcctgc
agcctgaagattttgcaacttattactgtctacaagattccaattacccgctcactttcggcggagggacacgactggagatta
aaggtggcagcggacctaaatcttgtgacaaaactcacacatgcccaccgtgcccagcacctgaactcctggggggacc
gtcagtcttcctcttccccccaaaacccaaggacaccctcatgatctcccggacccctgaggtcacatgcgtggtggtggac
gtgagccacgaagaccctgaggtcaagttcaactggtacgtggacggcgtggaggtgcataatgccaagacaaagccgc
ggggaggagcagtacaacagcacgtaccgtgtggtcagcgtcctcaccgtcctgcaccaggactggctgaatggcaagga
gtacaagtgcaaggtctccaacaaagcccttcccagccccatcgagaaaaccatctccaaagccaaagggcagccccga
gaaccacaggtgtacaccctgcccccatcccgggatgagctgaccaagaaccaggtcagcctgacgtgcctggtcaaag
gcttctatcccagcgacatcgccgtggagtgggagagcaatgggcagccggagaacaactacaagaccacgcctcccgt
gctggactccgacggctccttcatcctctacagcaagctcaccgtggacaagagcagatggcagcaggggaacgtcttctc
atgctccgtgatgcatgaggctctgcacaaccactacacgcagaagagcctctccctgtctccgggtaaatagtag SEQ ID No. 18: Human TGFβ1
ALDTNYCFSSTEKNCCVRQLYIDFRKDLGWKWIHEPKGYHANFCLGPCPYIW
SLDTQYSKVLALYNQHNPGASAAPCCVPQALEPLPIVYYVGRKPKVEQLSNM
IVRSCKCS

SEQUENCE LISTING

SEQ ID No. 19
GSSGG

SEQ ID No. 20
GGSG

SEQ ID No. 21
CPPCP

SEQ ID No. 22
SYGMH

SEQ ID No. 23
VISYDGSIKYYADSVKG

SEQ ID No. 24
TGEYSGYDTSGVEL

SEQ ID No. 25
TGEYSGYDTDPQYS

SEQ ID No. 26
TGFYSGYDTPASPD

SEQ ID No. 27
RASQGIGDDLG

SEQ ID No. 28
GTSTLQS

SEQ ID No. 29
LQDSNYPLT

SEQ ID No. 30
TGX$_1$YSGYDTX$_2$X$_3$X$_4$X$_5$X$_6$

The invention claimed is:

1. An isolated binding protein that binds TGFβ1, wherein the isolated binding protein is a dimer formed from a polypeptide chain having the formula of, from N-terminus to C-terminus:

(VH domain)-(linker1)-(VL domain)-(linker2)-
(hinge)-(Fc region), wherein
the VH domain comprises a heavy chain complementarity determining region (HCDR) 1 having the amino acid sequence of SEQ ID NO: 22, an HCDR2 having the amino acid sequence of SEQ ID NO: 23, and an HCDR3 having the amino acid sequence of SEQ ID NO: 24, 25, 26, or 30; and the VL domain comprises a light chain complementarity determining region (LCDR) 1 having the amino acid sequence of SEQ ID NO: 27 or the amino acid sequence of SEQ ID NO: 27 with an A2S substitution, an LCDR2 having the amino acid sequence of SEQ ID NO: 28, and an LCDR3 having the amino acid sequences of SEQ ID NO: 29;
the linker1 is a [G$_4$S]$_3$-type linker;
the linker2 is SEQ ID NO: 20 or a variant thereof, wherein the variant differs from SEQ ID NO: 20 in length by one to four amino acids, or differs from SEQ ID NO: 20 by having up to two amino acid substitutions from glycine to serine or from serine to glycine; and
the hinge comprises an amino acid sequence from a human IgG$_1$ or IgG$_4$ hinge region, or the amino acid sequence of SEQ ID NO: 7 or 21.

2. The isolated binding protein of claim 1, wherein
the VH domain comprises the human VH domain sequence set forth in SEQ ID NO: 1 or 2, or a variant thereof having up to four amino acid modifications; and
the VL domain comprises the human Vκ domain sequence set forth in SEQ ID NO: 5 or 6, or a variant thereof having up to four amino acid modifications.

3. The isolated binding protein of claim 2, wherein the VH and VL domains comprise the amino acid sequences set forth in SEQ ID NOs: 1 and 5, respectively.

4. The isolated binding protein of claim 1, wherein the linker1 comprises the amino acid sequence SGGGSGGGGSGGGGS (SEQ ID NO: 3) or GGGGSGGGGSGGGGS (SEQ ID NO: 4).

5. The isolated binding protein of claim 1, wherein the linker2 is SEQ ID NO: 20.

6. The isolated binding protein of claim 1, wherein the Fc region is derived from a human IgG$_1$, a human IgG$_4$, or a variant of a human IgG$_1$ or IgG$_4$ wherein up to ten amino acids are modified.

7. The isolated binding protein of claim 1, wherein the polypeptide chain comprises the amino acid sequence set forth in SEQ ID NO: 9.

8. The isolated binding protein of claim 1, wherein the isolated binding protein has at least one of the following characteristics:
   a) binding selectively to TGFβ1;
   b) having an $IC_{50}$ to human TGFβ1 of less than 1 nM in an A549 bioassay;
   c) exhibiting a Kd for human TGFβ1 at least about 50% lower than a Kd for human TGFβ2 as measured by surface plasmon resonance; and
   d) exhibiting a Kd for human TGFβ1 at least about 50% lower than a Kd for human TGFβ3 as measured by surface plasmon resonance.

9. A pharmaceutical composition comprising the isolated binding protein of claim 1 and a pharmaceutically acceptable excipient.

10. A method of treating a disease in a human in need of inhibition of TGFβ1 activity, comprising administering to the human a therapeutically effective amount of the isolated binding protein of claim 1.

11. The method of claim 10, wherein the disease is selected from the group consisting of a fibrotic disease, cancer, and an immune-mediated disease.

12. The method of claim 10, wherein the disease is diffuse cutaneous systemic sclerosis, bone remodeling disease, or kidney disease.

* * * * *

SEQUENCE LISTING

<160> NUMBER OF SEQ ID NOS: 30

<210> SEQ ID NO 1
<211> LENGTH: 123
<212> TYPE: PRT
<213> ORGANISM: Homo sapiens

<400> SEQUENCE: 1

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser
        115                 120

```
<210> SEQ ID NO 2
<211> LENGTH: 123
<212> TYPE: PRT
<213> ORGANISM: Homo sapiens

<400> SEQUENCE: 2

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Glu Leu Glu Trp Val
            35                  40                  45

Ala Val Ile Ser Tyr Asp Gly Ser Ile Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Pro Ala Ser Pro Asp
            100                 105                 110

Trp Gly Gln Gly Thr Thr Val Thr Val Ser Ser
        115                 120

<210> SEQ ID NO 3
<211> LENGTH: 15
<212> TYPE: PRT
<213> ORGANISM: Artificial Sequence
<220> FEATURE:
<223> OTHER INFORMATION: Synthetic

<400> SEQUENCE: 3

Ser Gly Gly Gly Ser Gly Gly Gly Ser Gly Gly Gly Ser
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Synthetic

<400> SEQUENCE: 4

Gly Gly Gly Gly Ser Gly Gly Gly Ser Gly Gly Gly Ser
1               5                   10                  15

<210> SEQ ID NO 5
<211> LENGTH: 107
<212> TYPE: PRT
<213> ORGANISM: Homo sapiens

<400> SEQUENCE: 5

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asp Asp
                20                  25                  30

Leu Gly Trp Tyr Gln Gln Lys Pro Gly Lys Ala Pro Ile Leu Leu Ile
            35                  40                  45

Tyr Gly Thr Ser Thr Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
65                  70                  75                  80
```

```
Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105

<210> SEQ ID NO 6
<211> LENGTH: 107
<212> TYPE: PRT
<213> ORGANISM: Homo sapiens

<400> SEQUENCE: 6

Glu Ile Val Leu Thr Gln Ser Pro Ser Leu Ser Ala Ser Val Gly
1               5                   10                  15

Asp Arg Val Thr Ile Thr Cys Arg Ser Ser Gln Gly Ile Gly Asp Asp
                20                  25                  30

Leu Gly Trp Tyr Gln Gln Lys Pro Gly Lys Ala Pro Ile Leu Leu Ile
            35                  40                  45

Tyr Gly Thr Ser Thr Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Leu Gln Asp Ser Asn Tyr Pro Leu
                85                  90                  95

Thr Phe Gly Gly Gly Thr Arg Leu Glu Ile Lys
            100                 105

<210> SEQ ID NO 7
<211> LENGTH: 22
<212> TYPE: PRT
<213> ORGANISM: Homo sapiens

<400> SEQUENCE: 7

Pro Lys Ser Cys Asp Lys Thr His Thr Cys Pro Pro Cys Pro Ala Pro
1               5                   10                  15

Glu Leu Leu Gly Gly Pro
            20

<210> SEQ ID NO 8
<211> LENGTH: 209
<212> TYPE: PRT
<213> ORGANISM: Homo sapiens

<400> SEQUENCE: 8

Ser Val Phe Leu Phe Pro Pro Lys Pro Lys Asp Thr Leu Met Ile Ser
1               5                   10                  15

Arg Thr Pro Glu Val Thr Cys Val Val Val Asp Val Ser His Glu Asp
                20                  25                  30

Pro Glu Val Lys Phe Asn Trp Tyr Val Asp Gly Val Glu Val His Asn
            35                  40                  45

Ala Lys Thr Lys Pro Arg Glu Glu Gln Tyr Asn Ser Thr Tyr Arg Val
50                  55                  60

Val Ser Val Leu Thr Val Leu His Gln Asp Trp Leu Asn Gly Lys Glu
65                  70                  75                  80

Tyr Lys Cys Lys Val Ser Asn Lys Ala Leu Pro Ala Pro Ile Glu Lys
                85                  90                  95

Thr Ile Ser Lys Ala Lys Gly Gln Pro Arg Glu Pro Gln Val Tyr Thr
            100                 105                 110
```

```
Leu Pro Pro Ser Arg Asp Glu Leu Thr Lys Asn Gln Val Ser Leu Thr
            115                 120                 125

Cys Leu Val Lys Gly Phe Tyr Pro Ser Asp Ile Ala Val Glu Trp Glu
    130                 135                 140

Ser Asn Gly Gln Pro Glu Asn Asn Tyr Lys Thr Thr Pro Pro Val Leu
145                 150                 155                 160

Asp Ser Asp Gly Ser Phe Phe Leu Tyr Ser Lys Leu Thr Val Asp Lys
                165                 170                 175

Ser Arg Trp Gln Gln Gly Asn Val Phe Ser Cys Ser Val Met His Glu
                180                 185                 190

Ala Leu His Asn His Tyr Thr Gln Lys Ser Leu Ser Leu Ser Pro Gly
            195                 200                 205

Lys
```

```
<210> SEQ ID NO 9
<211> LENGTH: 480
<212> TYPE: PRT
<213> ORGANISM: Homo sapiens

<400> SEQUENCE: 9

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Ser Gly Gly Gly Ser
        115                 120                 125

Gly Gly Gly Gly Ser Gly Gly Gly Ser Glu Ile Val Leu Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Gly Ile Gly Asp Asp Leu Gly Trp Tyr Gln Gln
                165                 170                 175

Lys Pro Gly Lys Ala Pro Ile Leu Leu Ile Tyr Gly Thr Ser Thr Leu
            180                 185                 190

Gln Ser Gly Val Pro Ser Arg Phe Ser Gly Ser Gly Ser Gly Thr Asp
        195                 200                 205

Phe Thr Leu Thr Ile Asn Ser Leu Gln Pro Glu Asp Phe Ala Thr Tyr
    210                 215                 220

Tyr Cys Leu Gln Asp Ser Asn Tyr Pro Leu Thr Phe Gly Gly Gly Thr
225                 230                 235                 240

Arg Leu Glu Ile Lys Gly Gly Ser Gly Pro Lys Ser Cys Asp Lys Thr
                245                 250                 255

His Thr Cys Pro Pro Cys Pro Ala Pro Glu Leu Leu Gly Gly Pro Ser
            260                 265                 270
```

-continued

Val Phe Leu Phe Pro Pro Lys Pro Lys Asp Thr Leu Met Ile Ser Arg
            275                 280                 285

Thr Pro Glu Val Thr Cys Val Val Asp Val Ser His Glu Asp Pro
290                 295                 300

Glu Val Lys Phe Asn Trp Tyr Val Asp Gly Val Glu Val His Asn Ala
305                 310                 315                 320

Lys Thr Lys Pro Arg Glu Glu Gln Tyr Asn Ser Thr Tyr Arg Val Val
                325                 330                 335

Ser Val Leu Thr Val Leu His Gln Asp Trp Leu Asn Gly Lys Glu Tyr
            340                 345                 350

Lys Cys Lys Val Ser Asn Lys Ala Leu Pro Ala Pro Ile Glu Lys Thr
            355                 360                 365

Ile Ser Lys Ala Lys Gly Gln Pro Arg Glu Pro Gln Val Tyr Thr Leu
370                 375                 380

Pro Pro Ser Arg Asp Glu Leu Thr Lys Asn Gln Val Ser Leu Thr Cys
385                 390                 395                 400

Leu Val Lys Gly Phe Tyr Pro Ser Asp Ile Ala Val Glu Trp Glu Ser
                405                 410                 415

Asn Gly Gln Pro Glu Asn Asn Tyr Lys Thr Thr Pro Pro Val Leu Asp
            420                 425                 430

Ser Asp Gly Ser Phe Phe Leu Tyr Ser Lys Leu Thr Val Asp Lys Ser
            435                 440                 445

Arg Trp Gln Gln Gly Asn Val Phe Ser Cys Ser Val Met His Glu Ala
            450                 455                 460

Leu His Asn His Tyr Thr Gln Lys Ser Leu Ser Leu Ser Pro Gly Lys
465                 470                 475                 480

<210> SEQ ID NO 10
<211> LENGTH: 213
<212> TYPE: PRT
<213> ORGANISM: Homo sapiens

<400> SEQUENCE: 10

Glu Trp Leu Thr Gln Ser Pro Ser Ser Leu Ser Ala Ser Val Gly Asp
1               5                   10                  15

Arg Val Thr Ile Thr Cys Arg Ala Ser Gln Gly Ile Gly Asp Asp Leu
                20                  25                  30

Gly Trp Tyr Gln Gln Lys Pro Gly Lys Ala Pro Ile Leu Leu Ile Tyr
            35                  40                  45

Gly Thr Ser Thr Leu Gln Ser Gly Val Pro Ser Arg Phe Ser Gly Ser
        50                  55                  60

Gly Ser Gly Thr Asp Phe Thr Leu Thr Ile Asn Ser Leu Gln Pro Glu
65                  70                  75                  80

Asp Phe Ala Thr Tyr Tyr Cys Leu Gln Asp Ser Asn Tyr Pro Leu Thr
                85                  90                  95

Phe Gly Gly Gly Thr Arg Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

-continued

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 450
<212> TYPE: PRT
<213> ORGANISM: Homo sapiens

<400> SEQUENCE: 11

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Ser Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 12
<211> LENGTH: 245
<212> TYPE: PRT
<213> ORGANISM: Homo sapiens

<400> SEQUENCE: 12

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Thr Gly Glu Tyr Ser Gly Tyr Asp Thr Asp Pro Gln Tyr Ser
        100                 105                 110

Trp Gly Gln Gly Thr Thr Val Thr Val Ser Ser Gly Gly Gly Gly Ser
        115                 120                 125

Gly Gly Gly Gly Ser Gly Gly Gly Ser Glu Ile Val Leu Thr Gln
    130                 135                 140

Ser Pro Ser Ser Leu Ser Ala Ser Val Gly Asp Arg Val Thr Ile Thr
145                 150                 155                 160

Cys Arg Ser Ser Gln Gly Ile Gly Asp Asp Leu Gly Trp Tyr Gln Gln
            165                 170                 175

Lys Pro Gly Lys Ala Pro Ile Leu Leu Ile Tyr Gly Thr Ser Thr Leu
        180                 185                 190

Gln Ser Gly Val Pro Ser Arg Phe Ser Gly Ser Gly Ser Gly Thr Asp
    195                 200                 205

Phe Thr Leu Thr Ile Asn Ser Leu Gln Pro Glu Asp Phe Ala Thr Tyr
    210                 215                 220

Tyr Cys Leu Gln Asp Ser Asn Tyr Pro Leu Thr Phe Gly Gly Gly Thr
225                 230                 235                 240

Arg Leu Glu Ile Lys
            245

<210> SEQ ID NO 13
<211> LENGTH: 984
<212> TYPE: DNA
<213> ORGANISM: Homo sapiens

<400> SEQUENCE: 13

```
atgaccatga ttacgccaag ctttggagcc ttttttttgg agattttcaa cgtgaaaaaa      60
ttattattcg caattccttt agttgttcct ttctatgcgg cccagccggc catggccgag     120
gtgcagctgg tggagtctgg gggaggcgtg gtccagcctg gaggtccct gagactctcc      180
tgtgcagcct ctggattcac cttcagtagc tatggcatgc actgggtccg ccaggctcca     240
ggcaaggagc tggagtgggt ggcagttata tcatatgatg gaagtattaa atactatgca     300
gactccgtga agggccgatt caccatctcc agagacaatt ccaagaacac gctgtatctg     360
caaatgaaca gcctgagagc tgaggacacg gctgtgtatt actgtgcgcg aactggtgaa     420
tatagtggct acgatacgga ccccccagtac tcctggggc aagggaccac ggtcaccgtc     480
tcctcaggtt cctctggcgg tgaaattgtg ctgactcagt ctccatcctc cctgtctgca     540
tctgtaggag acagagtcac catcacttgc cggtcaagtc agggcattgg agatgatttg     600
ggctggtatc agcagaagcc agggaaagcc cctatcctcc tgatctatgg tacatccact     660
ttacaaagtg gggtcccgtc aaggttcagc ggcagtggat ctggcacaga tttcactctc     720
accatcaaca gcctgcagcc tgaagatttt gcaacttatt actgtctaca agattccaat     780
tacccgctca ctttcggcgg agggacacga ctggagatta acgtgcggc cgcacatcat     840
catcaccatc acggggccgc agaacaaaaa ctcatctcag aagaggatct gaatggggcc     900
gcatagtagc tcgagatcaa acgggctagc cagccagaac tcgccccgga agaccccgag     960
gatgtcgagc accaccacca ccac                                             984
```

<210> SEQ ID NO 14
<211> LENGTH: 262
<212> TYPE: PRT
<213> ORGANISM: Homo sapiens

<400> SEQUENCE: 14

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Glu Ser Ser Tyr
            20                  25                  30

Gly Met His Trp Val Arg Gln Ala Pro Gly Lys Glu Leu Glu Trp Val
        35                  40                  45

Ala Val Ile Ser Tyr Asp Gly Ser Ile Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Gly Glu Tyr Ser Gly Tyr Asp Thr Asp Pro Gln Tyr Ser
            100                 105                 110

Trp Gly Gln Gly Thr Thr Val Thr Val Ser Ser Gly Ser Ser Gly Gly
        115                 120                 125

Glu Ile Val Leu Thr Gln Ser Pro Ser Ser Leu Ser Ala Ser Val Gly
    130                 135                 140

Asp Arg Val Thr Ile Thr Cys Arg Ser Ser Gln Gly Ile Gly Asp Asp
145                 150                 155                 160
```

```
Leu Gly Trp Tyr Gln Gln Lys Pro Gly Lys Ala Pro Ile Leu Leu Ile
                165                 170                 175
Tyr Gly Thr Ser Thr Leu Gln Ser Gly Val Pro Ser Arg Phe Ser Gly
            180                 185                 190
Ser Gly Ser Gly Thr Asp Phe Thr Leu Thr Ile Asn Ser Leu Gln Pro
        195                 200                 205
Glu Asp Phe Ala Thr Tyr Tyr Cys Leu Gln Asp Ser Asn Tyr Pro Leu
    210                 215                 220
Thr Phe Gly Gly Gly Thr Arg Leu Glu Ile Lys Arg Ala Ala Ala His
225                 230                 235                 240
His His His His Gly Ala Ala Glu Gln Lys Leu Ile Ser Glu Glu
                245                 250                 255
Asp Leu Asn Gly Ala Ala
            260

<210> SEQ ID NO 15
<211> LENGTH: 984
<212> TYPE: DNA
<213> ORGANISM: Homo sapiens

<400> SEQUENCE: 15
gaggtgcagc tggtggagtc tgggggaggc gtggtccagc ctggagggtc cctgagactc    60
tcctgtgcag cctctggatt caccttcagt agctatggca tgcactgggt ccgccaggct   120
ccaggcaagg agctggagtg ggtggcagtt atatcatatg atggaagtat taaatactat   180
gcagactccg tgaagggccg attcaccatc tccagagaca attccaagaa cacgctgtat   240
ctgcaaatga acagcctgag agctgaggac acggctgtgt attactgtgc gcgaactggt   300
gaatatagtg gctacgatac ggaccccag tactcctggg gcaagggac cacggtcacc   360 gtctcctcaa gtggaggcgg ttcaggcgga ggtggcagcg gcggtggcgg atcggaaatt   420
gtgctgactc agtctccatc ctccctgtct gcatctgtag agacagagt caccatcact   480 tgccggtcaa gtcagggcat tggagatgat ttgggctggt atcagcagaa gccagggaaa   540
gcccctatcc tcctgatcta tggtacatcc actttacaaa gtggggtccc gtcaaggttc   600
agcggcagtg gatctggcac agatttcact ctcaccatca acagcctgca gcctgaagat   660
tttgcaactt attactgtct acaagattcc aattacccgc tcactttcgg cggagggaca   720
cgactggaga ttaaacgtgc ggccgcacat catcatcacc atcacgggc cgcagaacaa   780 aaactcatct cagaagagga tctgaatggg gccgcaccca agcccagtac ccccccaggt   840
tcttcaggcg aactgaagag actgctgaaa catctgaaag aactgctgaa aggcccgcgt   900
aaaggcgaac tggaagaact gctgaaacat ctgaaagaac tgctgaaagg cggtgcgccg   960
ggcggtcatc atcatcacca tcat                                          984

<210> SEQ ID NO 16
<211> LENGTH: 328
<212> TYPE: PRT
<213> ORGANISM: Homo sapiens

<400> SEQUENCE: 16

Glu Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Glu Leu Glu Trp Val
        35                  40                  45
```

```
Ala Val Ile Ser Tyr Asp Gly Ser Ile Lys Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Thr Gly Glu Tyr Ser Gly Tyr Asp Thr Asp Pro Gln Tyr Ser
            100                 105                 110
Trp Gly Gln Gly Thr Thr Val Thr Val Ser Ser Gly Gly Gly Gly Ser
        115                 120                 125
Gly Gly Gly Gly Ser Gly Gly Gly Ser Glu Ile Val Leu Thr Gln
130                 135                 140
Ser Pro Ser Ser Leu Ser Ala Ser Val Gly Asp Arg Val Thr Ile Thr
145                 150                 155                 160
Cys Arg Ser Ser Gln Gly Ile Gly Asp Asp Leu Gly Trp Tyr Gln Gln
                165                 170                 175
Lys Pro Gly Lys Ala Pro Ile Leu Leu Ile Tyr Gly Ser Thr Leu
            180                 185                 190
Gln Ser Gly Val Pro Ser Arg Phe Ser Gly Ser Gly Ser Gly Thr Asp
        195                 200                 205
Phe Thr Leu Thr Ile Asn Ser Leu Gln Pro Glu Asp Phe Ala Thr Tyr
    210                 215                 220
Tyr Cys Leu Gln Asp Ser Asn Tyr Pro Leu Thr Phe Gly Gly Gly Thr
225                 230                 235                 240
Arg Leu Glu Ile Lys Arg Ala Ala Ala His His His His His His Gly
                245                 250                 255
Ala Ala Glu Gln Lys Leu Ile Ser Glu Glu Asp Leu Asn Gly Ala Ala
            260                 265                 270
Pro Lys Pro Ser Thr Pro Pro Gly Ser Ser Gly Glu Leu Glu Glu Leu
        275                 280                 285
Leu Lys His Leu Lys Glu Leu Leu Lys Gly Pro Arg Lys Gly Glu Leu
    290                 295                 300
Glu Glu Leu Leu Lys His Leu Lys Glu Leu Leu Lys Gly Gly Ala Pro
305                 310                 315                 320
Gly Gly His His His His His His
                325

<210> SEQ ID NO 17
<211> LENGTH: 1446
<212> TYPE: DNA
<213> ORGANISM: Homo sapiens

<400> SEQUENCE: 17
gaggtgcagc tggtggagtc tgggggaggc gtggtccagc ctggaggtc cctgagactc        60 tcctgtgcag cctctggatt caccttcagt agctatggca tgcactgggt ccgccaggct      120
ccaggcaagg agctggagtg ggtggcagtt atatcatatg atggaagtat taaatactat      180
gcagactccg tgaagggccg attcaccatc tccagagaca attccaagaa cacgctgtat      240
ctgcaaatga acagcctgag agctgaggac acggctgtgt attactgtgc gcgaactggg      300
gaatatagtg gctacgatac ggaccccag tactcctggg ggcaagggac cacggtcacc      360
gtctcctcaa gtggaggcgg ttcaggcgga ggtggcagcg gcggtggcgg atcggaaatt      420
gtgctgactc agtctccatc ctccctgtct gcatctgtag gagacagagt caccatcact      480
tgccggtcaa gtcagggcat tggagatgat ttgggctggt atcagcagaa gccagggaaa      540
```

```
gcccctatcc tcctgatcta tggtacatcc actttacaaa gtggggtccc gtcaaggttc    600
agcggcagtg gatctggcac agatttcact ctcaccatca acagcctgca gcctgaagat    660
tttgcaactt attactgtct acaagattcc aattacccgc tcactttcgg cggagggaca    720
cgactggaga ttaaaggtgg cagcggacct aaatcttgtg acaaaactca cacatgccca    780
ccgtgcccag cacctgaact cctgggggga ccgtcagtct tcctcttccc cccaaaaccc    840
aaggacaccc tcatgatctc ccggacccct gaggtcacat gcgtggtggt ggacgtgagc    900
cacgaagacc ctgaggtcaa gttcaactgg tacgtggacg gcgtggaggt gcataatgcc    960
aagacaaagc cgcgggagga gcagtacaac agcacgtacc gtgtggtcag cgtcctcacc   1020
gtcctgcacc aggactggct gaatggcaag gagtacaagt gcaaggtctc caacaaagcc   1080
ctcccagccc ccatcgagaa aaccatctcc aaagccaaag gcagccccg agaaccacag    1140 gtgtacaccc tgcccccatc ccgggatgag ctgaccaaga accaggtcag cctgacgtgc   1200
ctggtcaaag gcttctatcc cagcgacatc gccgtggagt gggagagcaa tgggcagccg   1260
gagaacaact acaagaccac gcctcccgtg ctggactccg acggctcctt cttcctctac   1320
agcaagctca ccgtggacaa gagcagatgg cagcagggga acgtcttctc atgctccgtg   1380
atgcatgagg ctctgcacaa ccactacacg cagaagagcc tctccctgtc tccgggtaaa   1440
tagtag                                                             1446
```

```
<210> SEQ ID NO 18
<211> LENGTH: 112
<212> TYPE: PRT
<213> ORGANISM: Homo sapiens

<400> SEQUENCE: 18

Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110

<210> SEQ ID NO 19
<211> LENGTH: 5
<212> TYPE: PRT
<213> ORGANISM: Homo sapiens

<400> SEQUENCE: 19

Gly Ser Ser Gly Gly
1               5

<210> SEQ ID NO 20
<211> LENGTH: 4
<212> TYPE: PRT
<213> ORGANISM: Homo sapiens
```

```
<400> SEQUENCE: 20

Gly Gly Ser Gly
1

<210> SEQ ID NO 21
<211> LENGTH: 5
<212> TYPE: PRT
<213> ORGANISM: Homo sapiens

<400> SEQUENCE: 21

Cys Pro Pro Cys Pro
1               5

<210> SEQ ID NO 22
<211> LENGTH: 5
<212> TYPE: PRT
<213> ORGANISM: Homo sapiens

<400> SEQUENCE: 22

Ser Tyr Gly Met His
1               5

<210> SEQ ID NO 23
<211> LENGTH: 17
<212> TYPE: PRT
<213> ORGANISM: Homo sapiens

<400> SEQUENCE: 23

Val Ile Ser Tyr Asp Gly Ser Ile Lys Tyr Tyr Ala Asp Ser Val Lys
1               5                   10                  15

Gly

<210> SEQ ID NO 24
<211> LENGTH: 14
<212> TYPE: PRT
<213> ORGANISM: Homo sapiens

<400> SEQUENCE: 24

Thr Gly Glu Tyr Ser Gly Tyr Asp Thr Ser Gly Val Glu Leu
1               5                   10

<210> SEQ ID NO 25
<211> LENGTH: 14
<212> TYPE: PRT
<213> ORGANISM: Homo sapiens

<400> SEQUENCE: 25

Thr Gly Glu Tyr Ser Gly Tyr Asp Thr Asp Pro Gln Tyr Ser
1               5                   10

<210> SEQ ID NO 26
<211> LENGTH: 14
<212> TYPE: PRT
<213> ORGANISM: Homo sapiens

<400> SEQUENCE: 26

Thr Gly Phe Tyr Ser Gly Tyr Asp Thr Pro Ala Ser Pro Asp
1               5                   10

<210> SEQ ID NO 27
<211> LENGTH: 11
<212> TYPE: PRT
<213> ORGANISM: Homo sapiens
```

```
<400> SEQUENCE: 27

Arg Ala Ser Gln Gly Ile Gly Asp Asp Leu Gly
1               5                   10

<210> SEQ ID NO 28
<211> LENGTH: 7
<212> TYPE: PRT
<213> ORGANISM: Homo sapiens

<400> SEQUENCE: 28

Gly Thr Ser Thr Leu Gln Ser
1               5

<210> SEQ ID NO 29
<211> LENGTH: 9
<212> TYPE: PRT
<213> ORGANISM: Homo sapiens

<400> SEQUENCE: 29

Leu Gln Asp Ser Asn Tyr Pro Leu Thr
1               5

<210> SEQ ID NO 30
<211> LENGTH: 14
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (10)..(14)
<223> OTHER INFORMATION: Xaa can be any naturally occurring amino acid

<400> SEQUENCE: 30

Thr Gly Xaa Tyr Ser Gly Tyr Asp Thr Xaa Xaa Xaa Xaa Xaa
1               5                   10
```